United States Patent
Konomura

(10) Patent No.: US 8,314,834 B2
(45) Date of Patent: Nov. 20, 2012

(54) ENDOSCOPE DEVICE

(75) Inventor: Yutaka Konomura, Tokyo (JP)

(73) Assignee: Olympus Corporation, Tokyo (JP)

( * ) Notice: Subject to any disclaimer, the term of this patent is extended or adjusted under 35 U.S.C. 154(b) by 311 days.

(21) Appl. No.: 12/400,665

(22) Filed: Mar. 9, 2009

(65) Prior Publication Data

US 2009/0201364 A1    Aug. 13, 2009

Related U.S. Application Data

(63) Continuation of application No. 11/637,500, filed on Dec. 12, 2006, now Pat. No. 7,518,632.

(30) Foreign Application Priority Data

Dec. 13, 2005   (JP) .................................. 2005-358562

(51) Int. Cl.
*H04N 7/18* (2006.01)
(52) U.S. Cl. ................ 348/65; 348/45; 348/47; 348/68; 348/46; 348/76; 348/69; 600/109; 600/118; 600/166; 600/178
(58) Field of Classification Search .............. 348/65, 348/45, 47, 68, 46, 76, 69; 600/109, 118, 600/166, 178
See application file for complete search history.

(56) References Cited

U.S. PATENT DOCUMENTS

| 4,812,643 | A | * | 3/1989 | Talbot | 250/222.1 |
| 5,568,271 | A | * | 10/1996 | Fukuchi et al. | 386/341 |
| 5,575,754 | A | * | 11/1996 | Konomura | 600/117 |
| 6,899,593 | B1 |   | 5/2005 | Moeller et al. |   |
| 6,945,931 | B2 | * | 9/2005 | Ogawa | 600/118 |
| 2004/0183900 | A1 | * | 9/2004 | Karpen et al. | 348/92 |

FOREIGN PATENT DOCUMENTS

| JP | 56-60843 A | 5/1981 |
| JP | 7-113749 A | 5/1995 |
| JP | H8-228993 | 9/1996 |
| JP | 2002-336188 | 11/2002 |

OTHER PUBLICATIONS

Notice of Allowance dated Nov. 8, 2011 from corresponding Japanese Patent Application No. JP 2005-358562 together with partial English language translation.

* cited by examiner

*Primary Examiner* — Shawn An
(74) *Attorney, Agent, or Firm* — Scully, Scott, Murphy & Presser, PC

(57) ABSTRACT

An endoscope device including an insertion part including an observation optical system and a measuring optical system, wherein the endoscope device is provided with a characteristic value comparing circuit which compares previous characteristic values and current characteristic values to identify previous characteristic values corresponding to the current characteristic values, and when storing the current characteristic values, current characteristic values corresponding to the previous characteristic values, identified by the characteristic value comparing circuit, are stored in a storage circuit together with various information. According to the invention, for inspecting turbine blades of jet engines, automation (labor-saving) of the inspection process by reducing the number of the inspection steps is realized and the difficulty in the inspection of analysis areas is eliminated.

17 Claims, 19 Drawing Sheets

ENDOSCOPE DEVICE

BACKGROUND OF THE INVENTION

1. Field of the Invention

The present invention relates to an endoscope device. This application relates to and claims priority from Japanese Patent Application No. 2005-358562, filed on Dec. 13, 2005, the entire disclosures of which are incorporated herein by reference.

2. Description of the Related Art

Recently, to inspect turbine blades of jet engines or the like, an endoscope device is used. For example, an endoscope device, of which an imaging part including a camera is inserted into a jet engine and extracts a line by an edge extraction method from a blade image captured by the imaging part and determines whether the turbine blades have defects from discontinuity of the extracted line, is provided (refer to US 2004/0183900A1). Such type of endoscope device uses a method in which, when a defect of the turbine blades exceeds a predetermined value, an inspection operator is informed of this by automated voice.

On the other hand, for inspecting the turbine blades, an inspection method is provided in which turbine blades are three-dimensionally captured (stereoscopically captured) from two positions shifted by an appropriate distance from each other, and it is determined whether the turbine blades have a defect based on the two captured photos (refer to Japanese Published Unexamined Patent Application No. H08-228993). An inspection method is also provided in which, from the blade images obtained by stereoscopically imaging the turbine blades according to the above-described inspection method, a line is extracted by an edge extraction method, and it is accurately determined whether the turbine blades have a defect or not (refer to Japanese Published Unexamined Patent Application No. 2002-336188).

SUMMARY OF THE INVENTION

An endoscope device according to the present invention includes an insertion part which is provided with an observation optical system which captures a plurality of analysis areas for observation. The insertion part also includes a measuring optical system which captures the analysis areas in order to be measured. The endoscope device includes: a numbering part which numbers observation images of each area captured by the observation optical system; a measuring part which extracts measuring information based on measuring images of each area captured by the measuring optical system; a first storage part which stores first analysis area information including the observation images numbered by the numbering part and corresponding measuring information of the analysis areas associated with the observation images extracted by the measuring part; a second storage part which stores second analysis area information including new observation images captured by the observation optical system and newly numbered by the numbering part and new measuring information of the corresponding analysis areas associated with the new observation images newly extracted by the measuring part; and an identifying recognition part which identifies the first analysis area information corresponding to the second analysis area information by comparing the first analysis area information and the second analysis area information. When the second storage part newly stores the second analysis area information, the first storage part stores the second analysis area information corresponding to the first analysis area information identified by the identifying recognition part in addition to the first analysis area information.

Preferably, in the endoscope device, the measuring optical system also serves as the observation optical system.

Preferably, in the endoscope device, the endoscope device includes a movement operating part which successively moves the analysis areas so that the analysis areas are captured by the observation optical system and by the measuring optical system. When the movement operating part moves one of a plurality of the analysis areas and when the movement operating part moves the plurality of the analysis areas so that the plurality of the analysis areas make one revolution, the movement operating part informs the measuring part or the numbering parts of this.

Preferably, in the endoscope device, the measuring part is provided with a characteristic extracting part which extracts multiple kinds of characteristics from the measuring information, and the first storage part and the second storage part store the multiple kinds of characteristics as a part of the measuring information.

Preferably, in the endoscope device, multiple kinds of characteristics to be extracted by the characteristic extracting part are cracks, fractures, dents, and damages including other deformations of the analysis area.

Preferably, in the endoscope device, the measuring part is provided with a characteristic value converting part which converts the multiple kinds of characteristics into multiple kinds of characteristic values, which was normally quantified by a predetermined evaluating calculation, and the first storage part and the second storage part store the multiple kinds of characteristic values as a part of the measuring information.

Preferably, in the endoscope device, the measuring part is provided with a comprehensive characteristic value deriving part which derives comprehensive characteristic values of the analysis areas by weighting and summing up the multiple kinds of characteristics, and the first storage part and the second storage part store the multiple kinds of comprehensive characteristic values as a part of the measuring information.

Preferably, in the endoscope device, the endoscope device includes an evaluating part which evaluates the first analysis area information and the second analysis area information.

Preferably, in the endoscope device, the endoscope device includes a judging part which determines whether the analysis areas are conforming or nonconforming based on the evaluation made by the evaluating part.

Preferably, in the endoscope device, the measuring optical system includes two or more imaging parts whose installation positions are shifted from each other, and stereoscopically captures the analysis areas.

Preferably, in the endo scope device, the measuring optical system includes an imaging part which captures the analysis area according to a light-section method, and stereoscopically captures the analysis area.

Preferably, in the endoscope device, the insertion part is provided with an illuminating part which illuminates an analysis area.

Preferably, in the endoscope device, the insertion part is provided with an elongated member which extends in parallel in an axial direction of the insertion part and is movable toward and away from the insertion part via a link member, and the elongated member is provided with an illuminating part, which is arranged in line in a longitudinal direction, which illuminates the analysis area.

Preferably, in the endoscope device, two or more sets of the measuring optical systems are provided in a longitudinal direction of the insertion part.

Preferably, in the endoscope device, the sets of the measuring optical systems are shifted from each other in a circumferential direction of the insertion part.

DETAILED DESCRIPTION OF THE INVENTION

Hereinafter, the best mode of an endoscope device of the present invention will be described with reference to the accompanying drawings.

Figure 1:
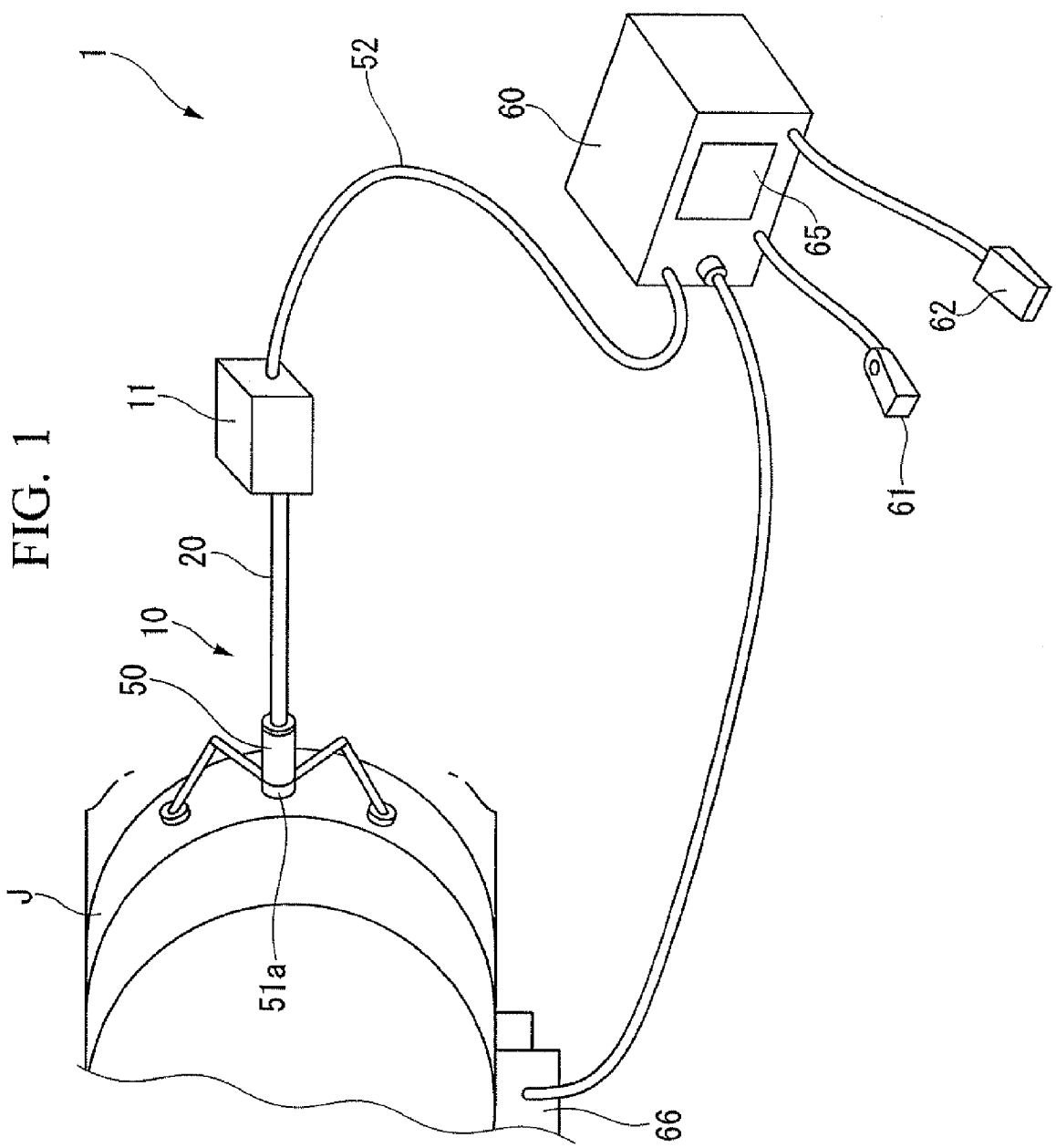
FIG. 1 is an entire external view of an endoscope device.
Figure 2:
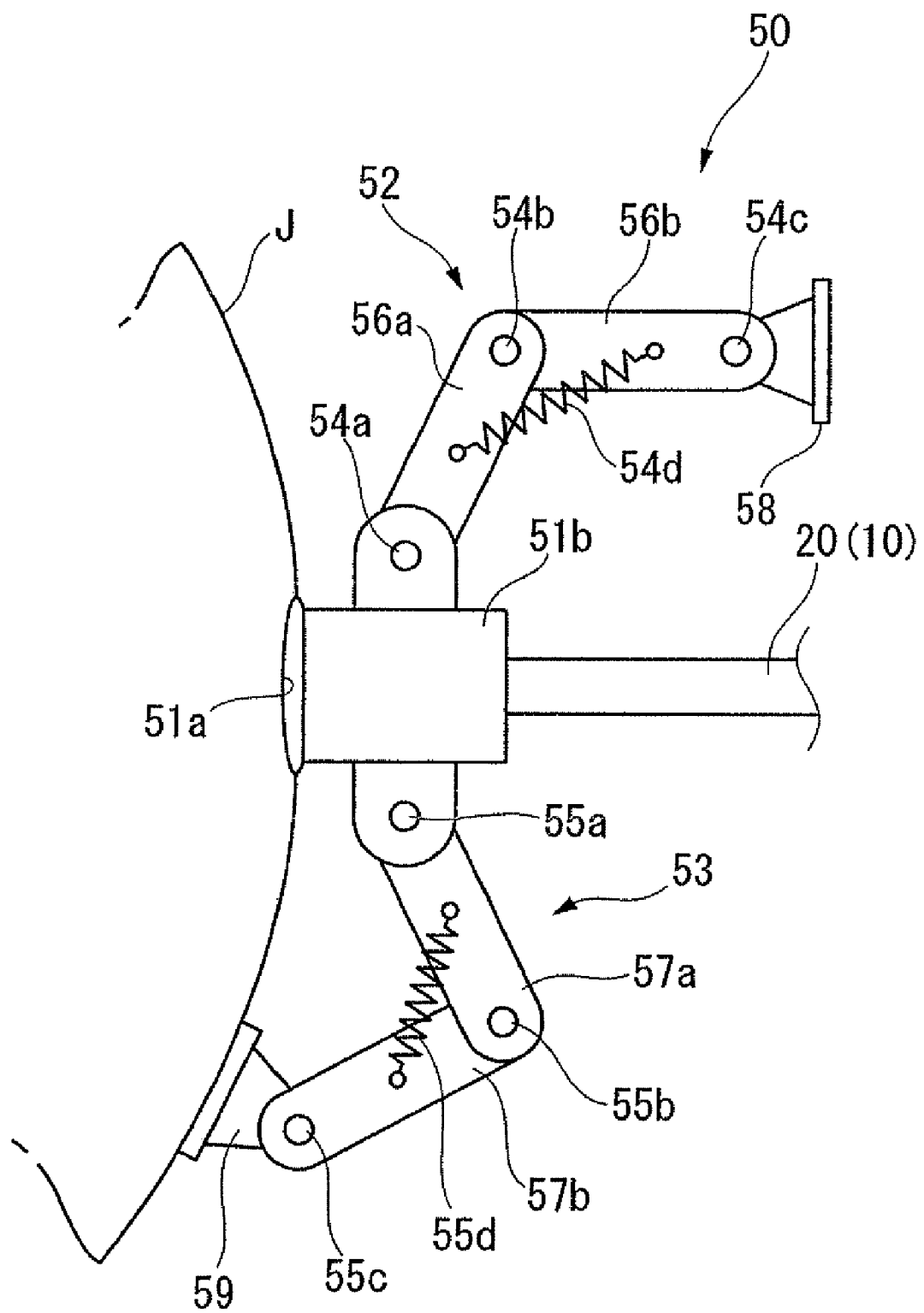
FIG. 2 is a side view showing details of a fixture.
Figure 3:
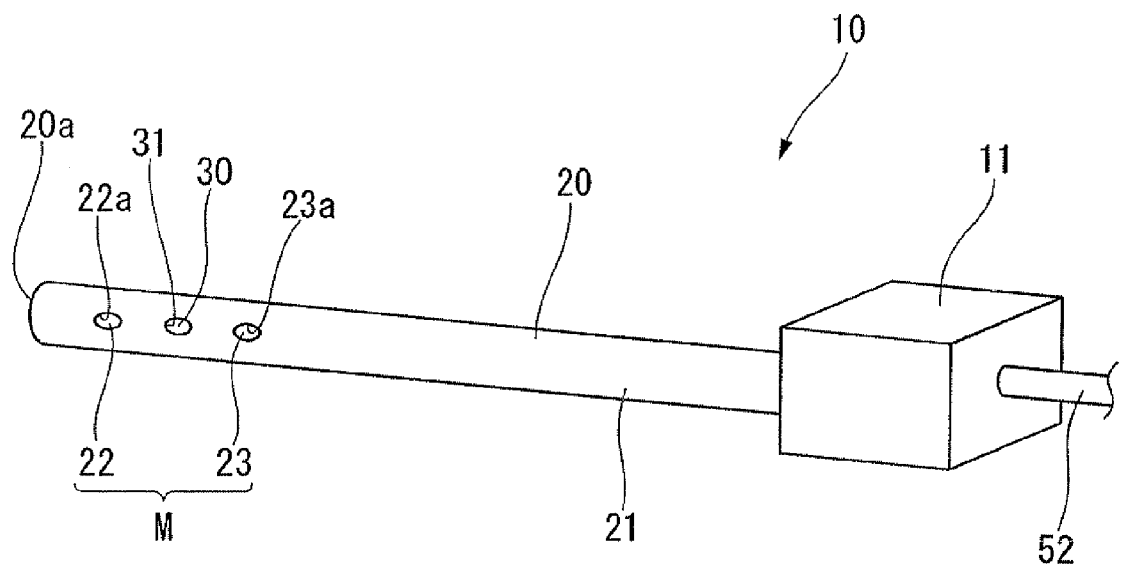
FIG. 3 is an external view of an endoscope.
Figure 4:
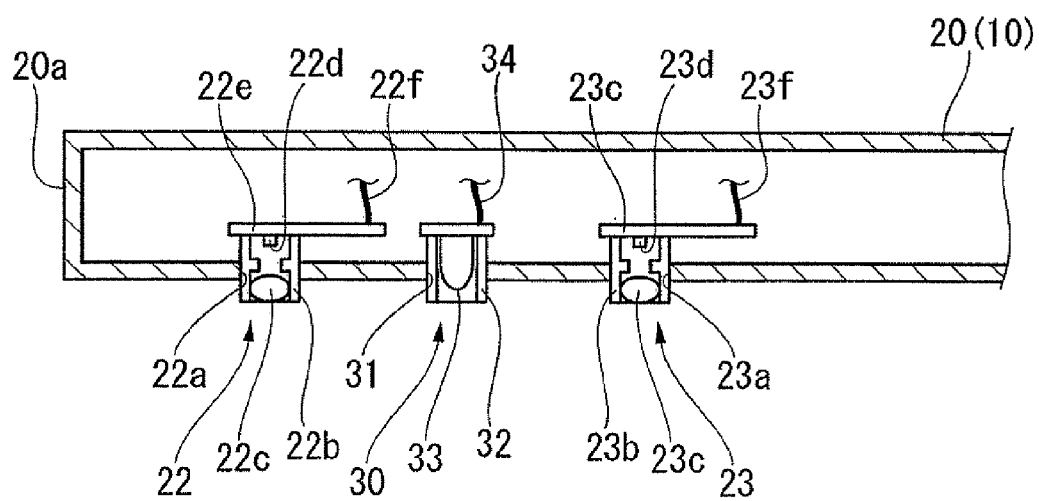
FIG. 4 is a sectional view of an insertion part of the endoscope of FIG. 3.
Figure 5:
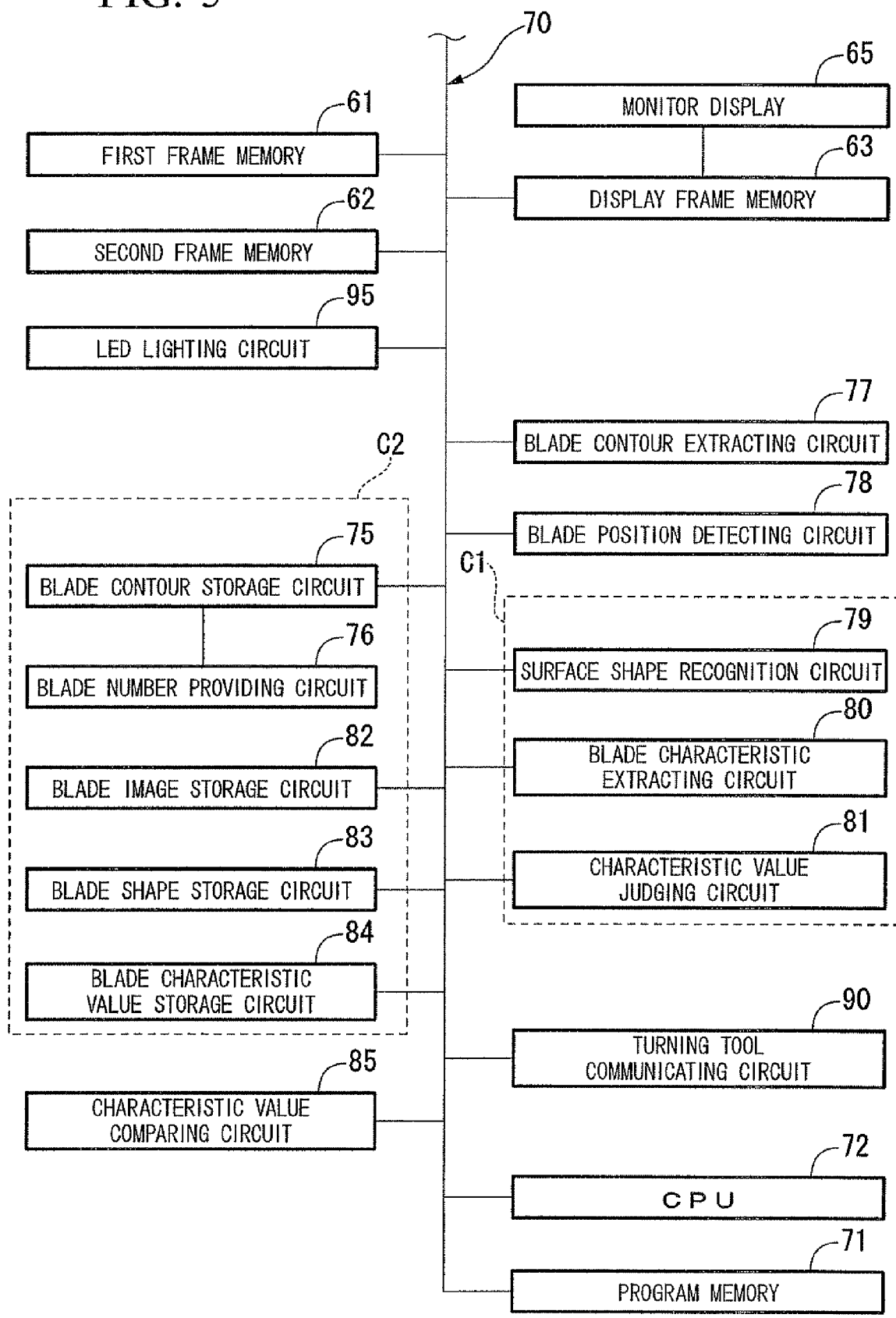
FIG. 5 is a block diagram of a controller.
Figure 6:
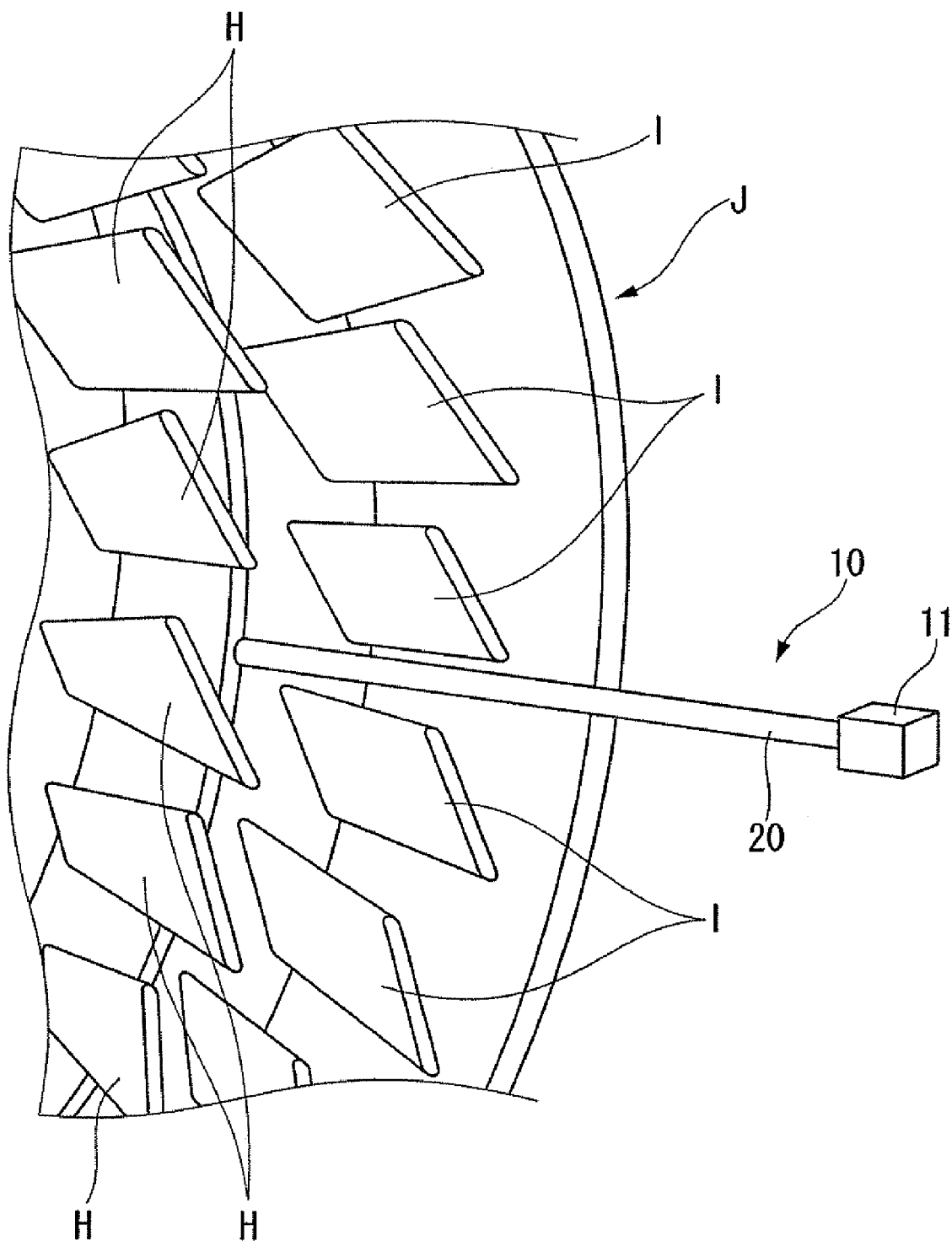
FIG. 6 is a drawing showing the insertion part of the endoscope inserted in a jet engine.
Figure 7A:
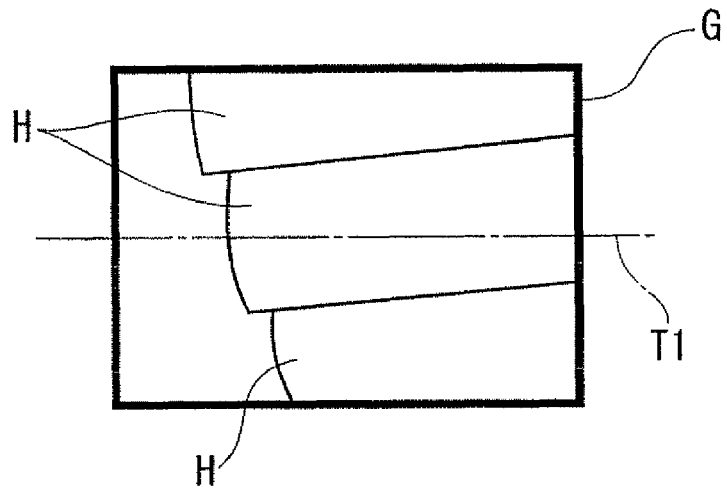
FIG. 7A is one of the drawings showing a positioning operation performed by a blade position detecting circuit.
Figure 7B:
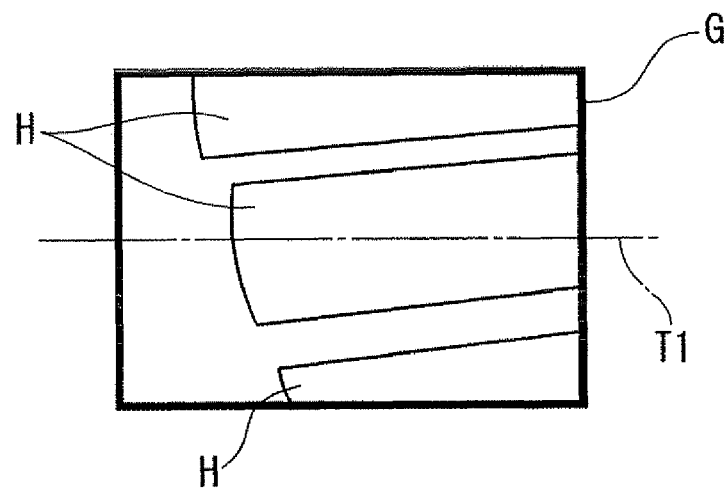
FIG. 7B is one of the drawings showing a positioning operation performed by a blade position detecting circuit.
Figure 7C:
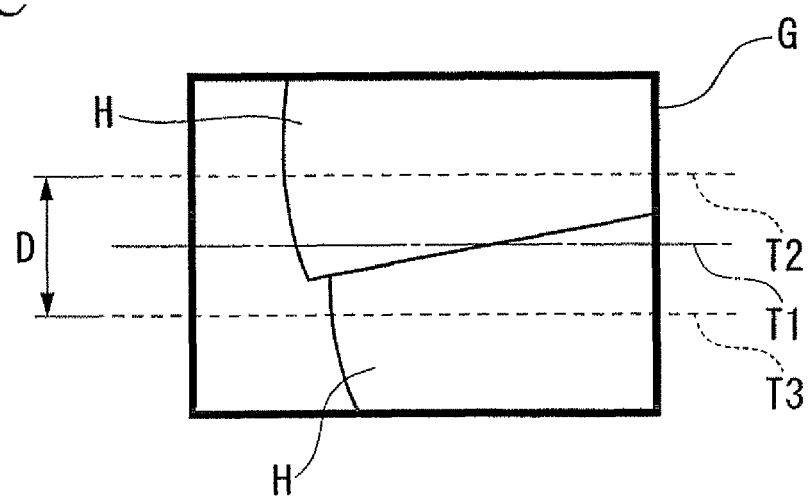
FIG. 7C is one of the drawings showing a positioning operation performed by a blade position detecting circuit.
Figure 8A:
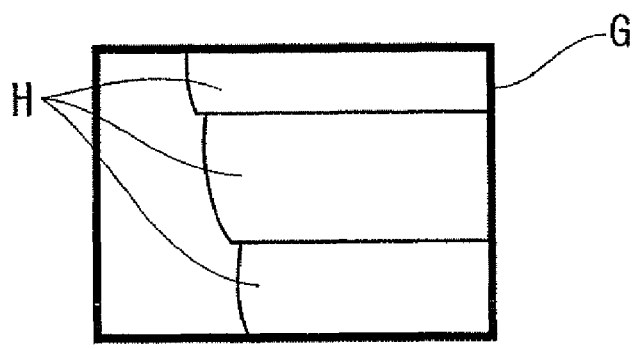
FIG. 8A is one of the drawings showing characteristic (damage) extraction performed by a blade characteristic extracting circuit.
Figure 8B:
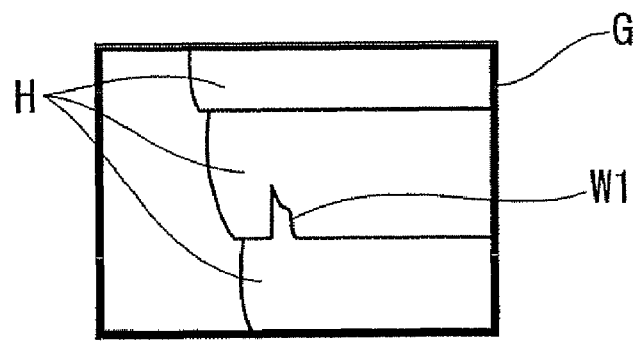
FIG. 8B is one of the drawings showing characteristic (damage) extraction performed by a blade characteristic extracting circuit.
Figure 9A:
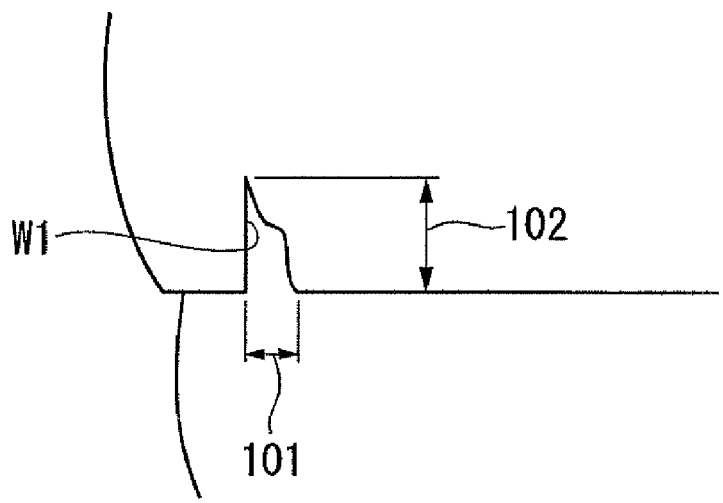
FIG. 9A is one of the drawings showing the details of the characteristic extraction of FIG. 8A to FIG. 8D.
Figure 9B:
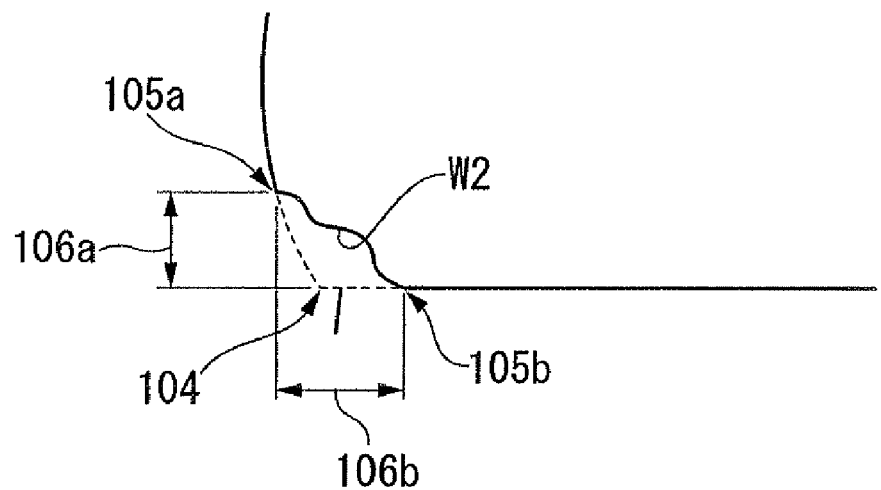
FIG. 9B is one of the drawings showing the details of the characteristic extraction of FIG. 8A to FIG. 8D.
Figure 9C:
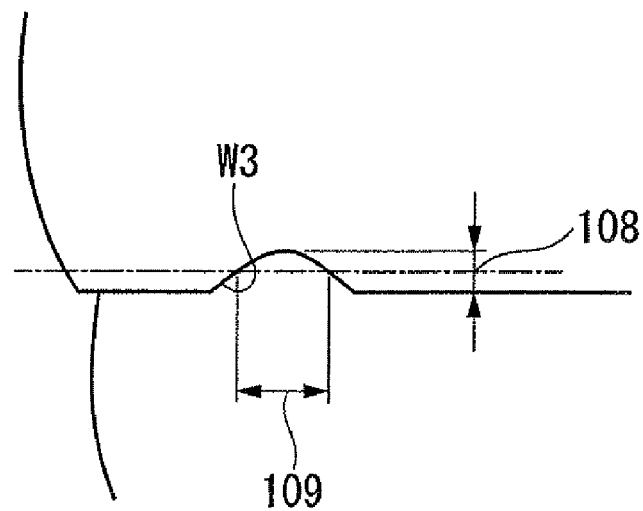
FIG. 9C is one of the drawings showing the details of the characteristic extraction of FIG. 8A to FIG. 8D.
Figure 10A:
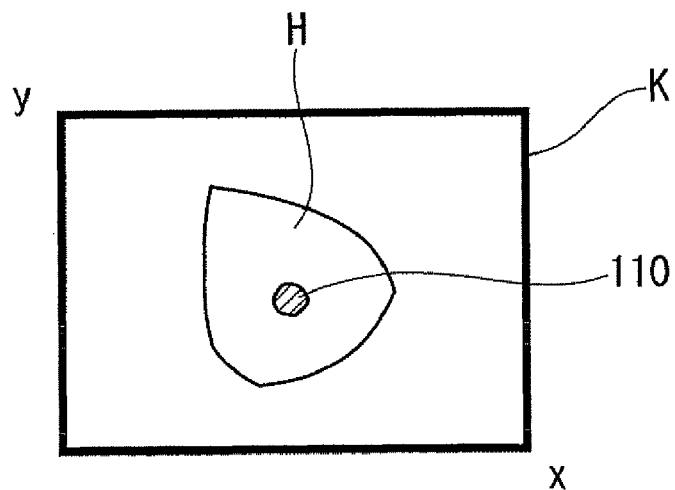
FIG. 10A is one of the drawings showing characteristic (stain) extraction performed by the blade characteristic extracting circuit.
Figure 10B:
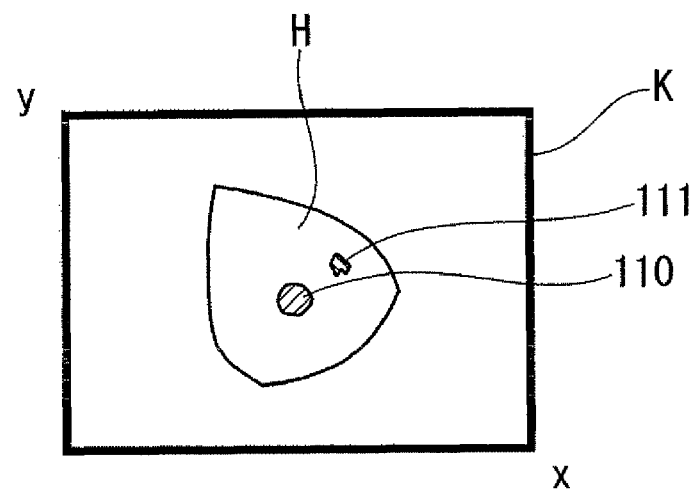
FIG. 10B is one of the drawings showing characteristic (stain) extraction performed by the blade characteristic extracting circuit.
Figure 10C:
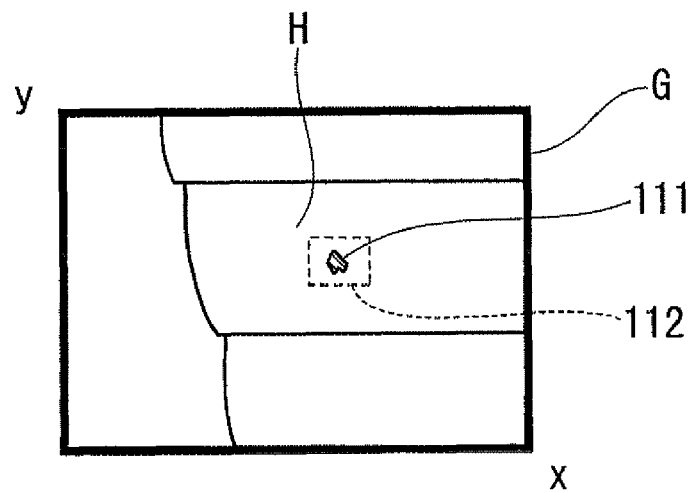
FIG. 10C is one of the drawings showing characteristic (stain) extraction performed by the blade characteristic extracting circuit.
Figure 11A:
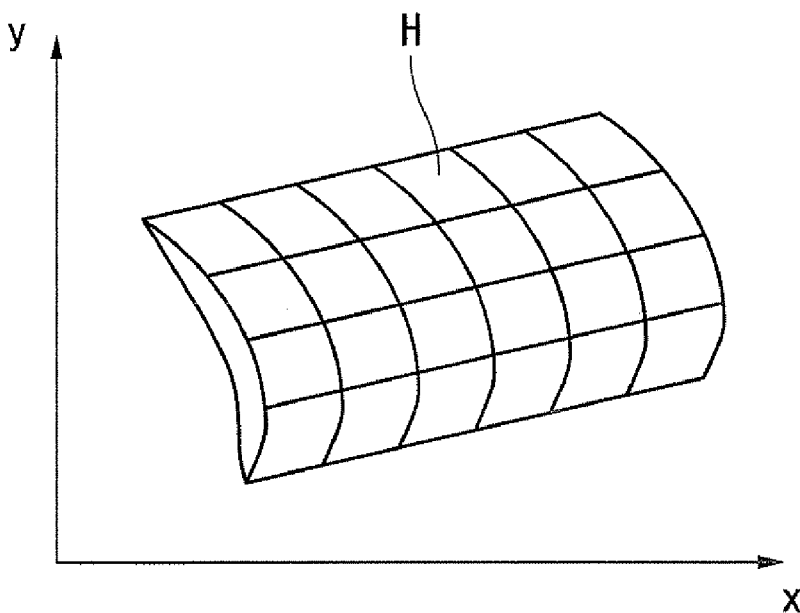
FIG. 11A is one of the drawings showing three-dimensional shape extraction performed by a surface shape recognition circuit.
Figure 11B:
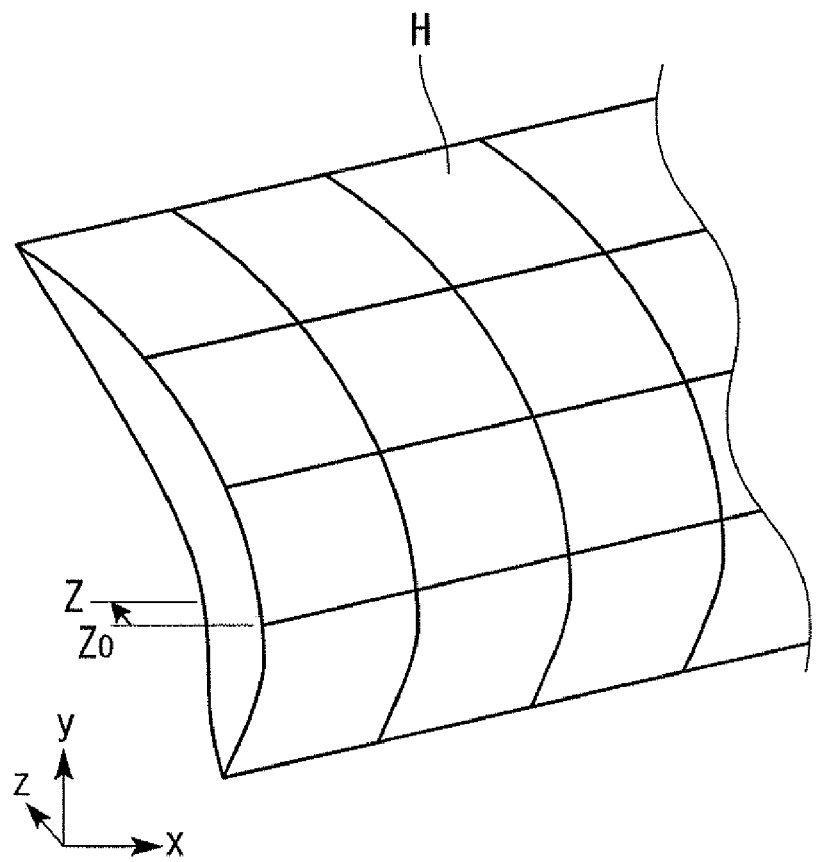
FIG. 11B is one of the drawings showing three-dimensional shape extraction performed by a surface shape recognition circuit.
Figure 12:
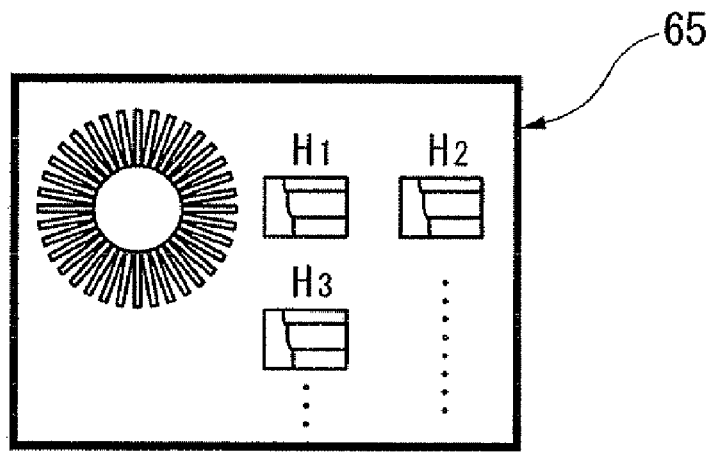
FIG. 12 is a drawing showing an example of a result of inspection.
Figure 13:
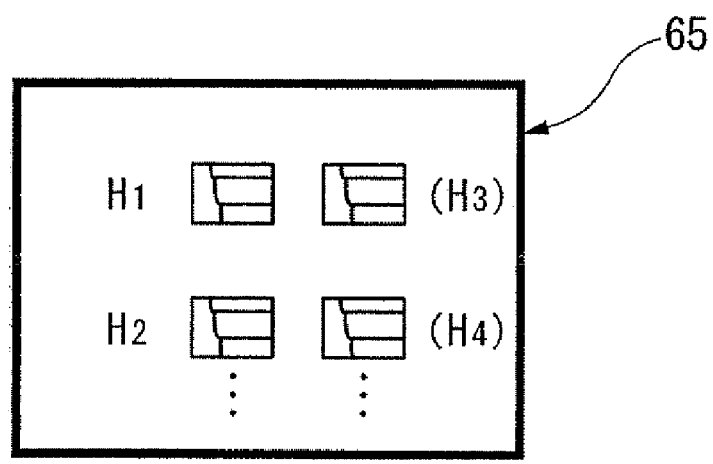
FIG. 13 is a drawing showing an example of a result of inspection.
Figure 14:
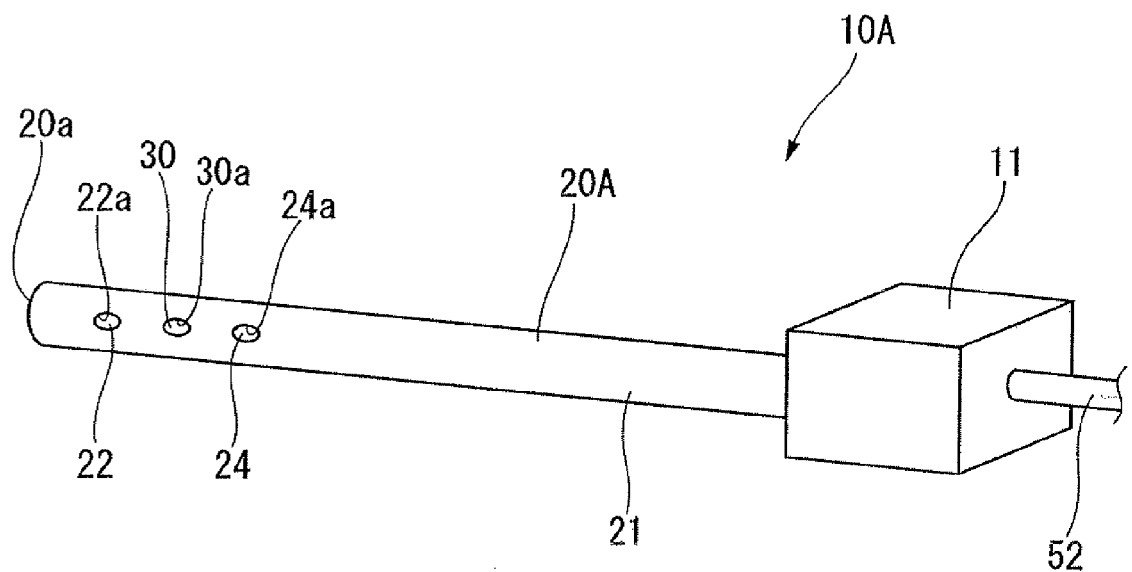
FIG. 14 is an external view showing another example of an endoscope.
Figure 15:
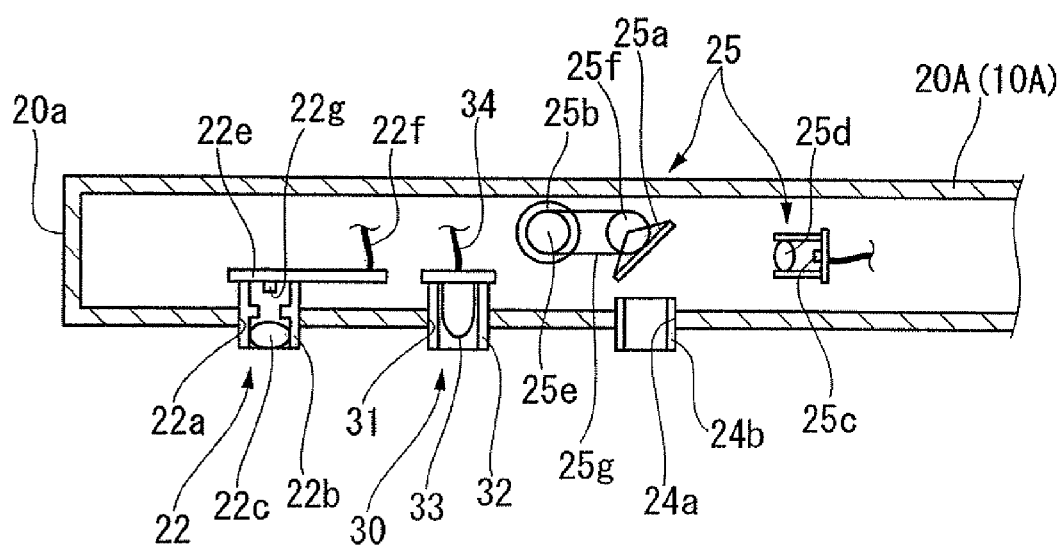
FIG. 15 is a sectional view of an insertion part of the endoscope of FIG. 14.
Figure 16:
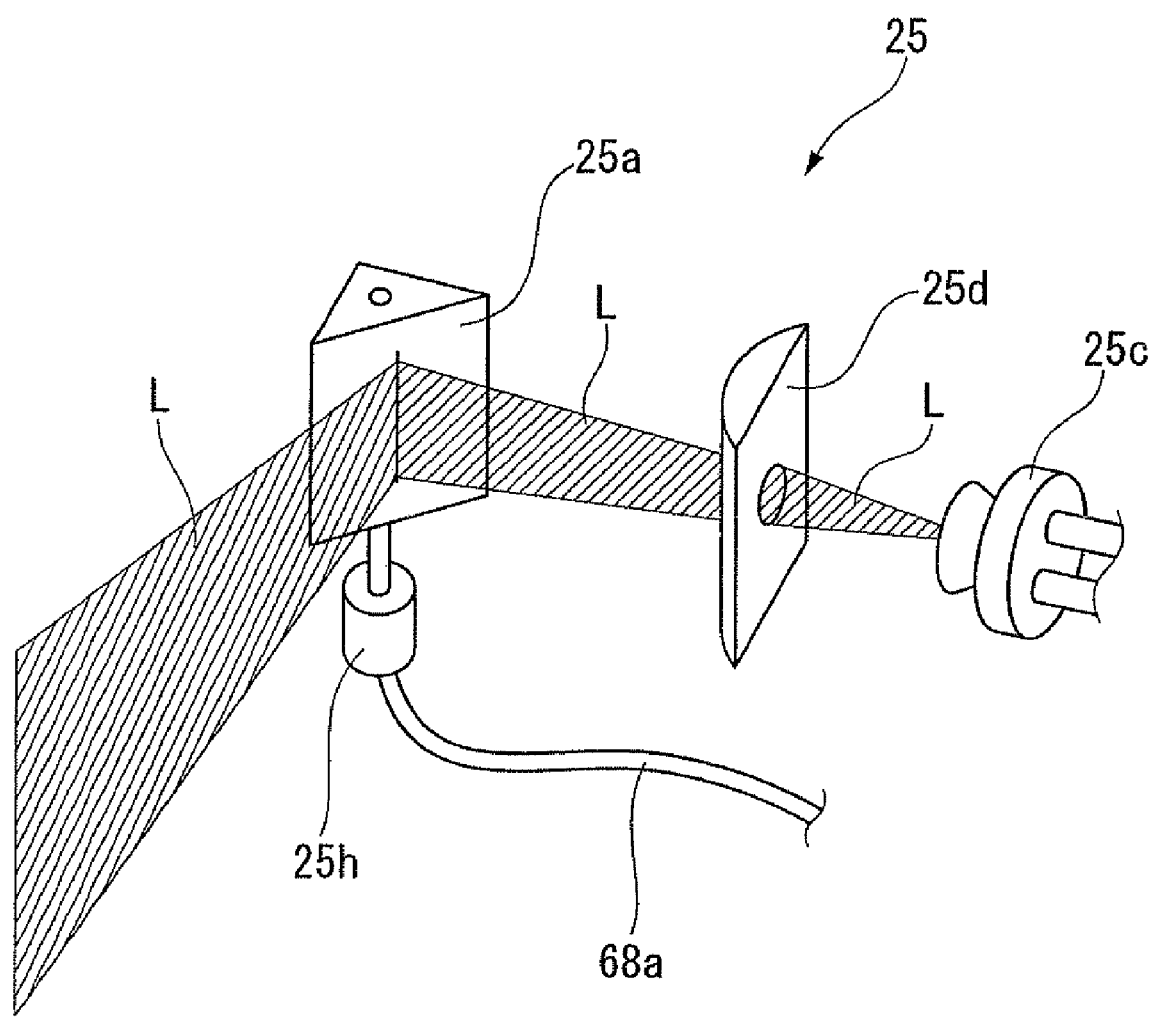
FIG. 16 is a perspective view of a laser line measuring device.
Figure 17:
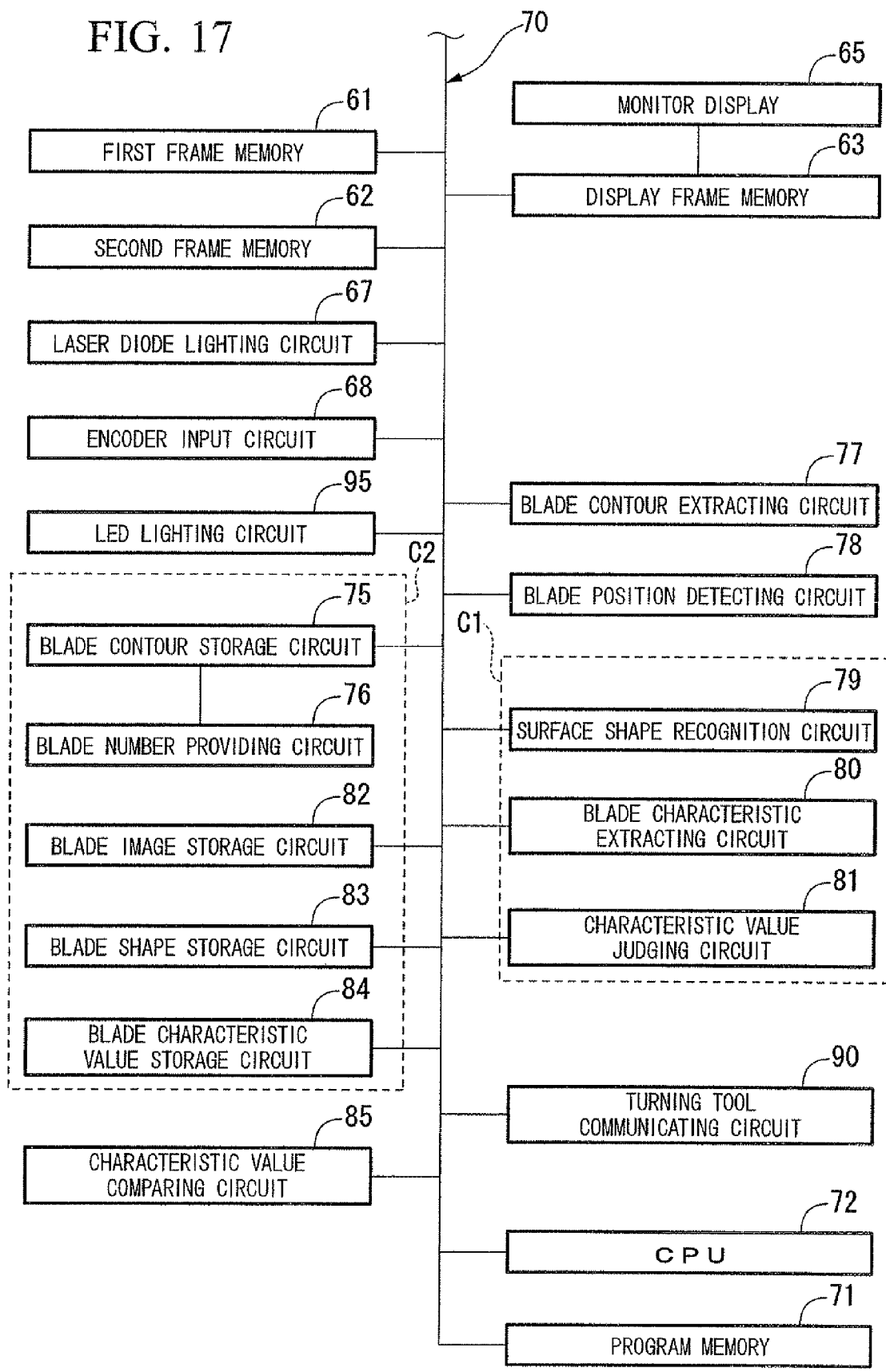
FIG. 17 is a block diagram showing the controller of FIG. 14.
Figure 18:
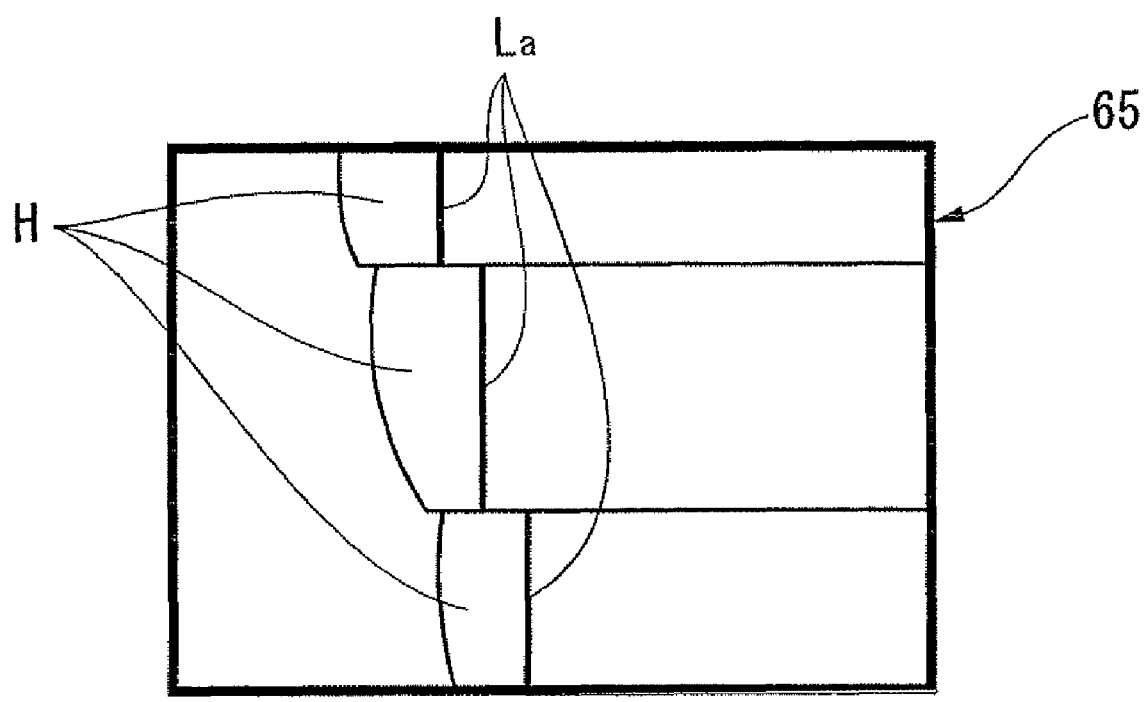
FIG. 18 is a display image of a blade irradiated with a laser beam.
Figure 19:
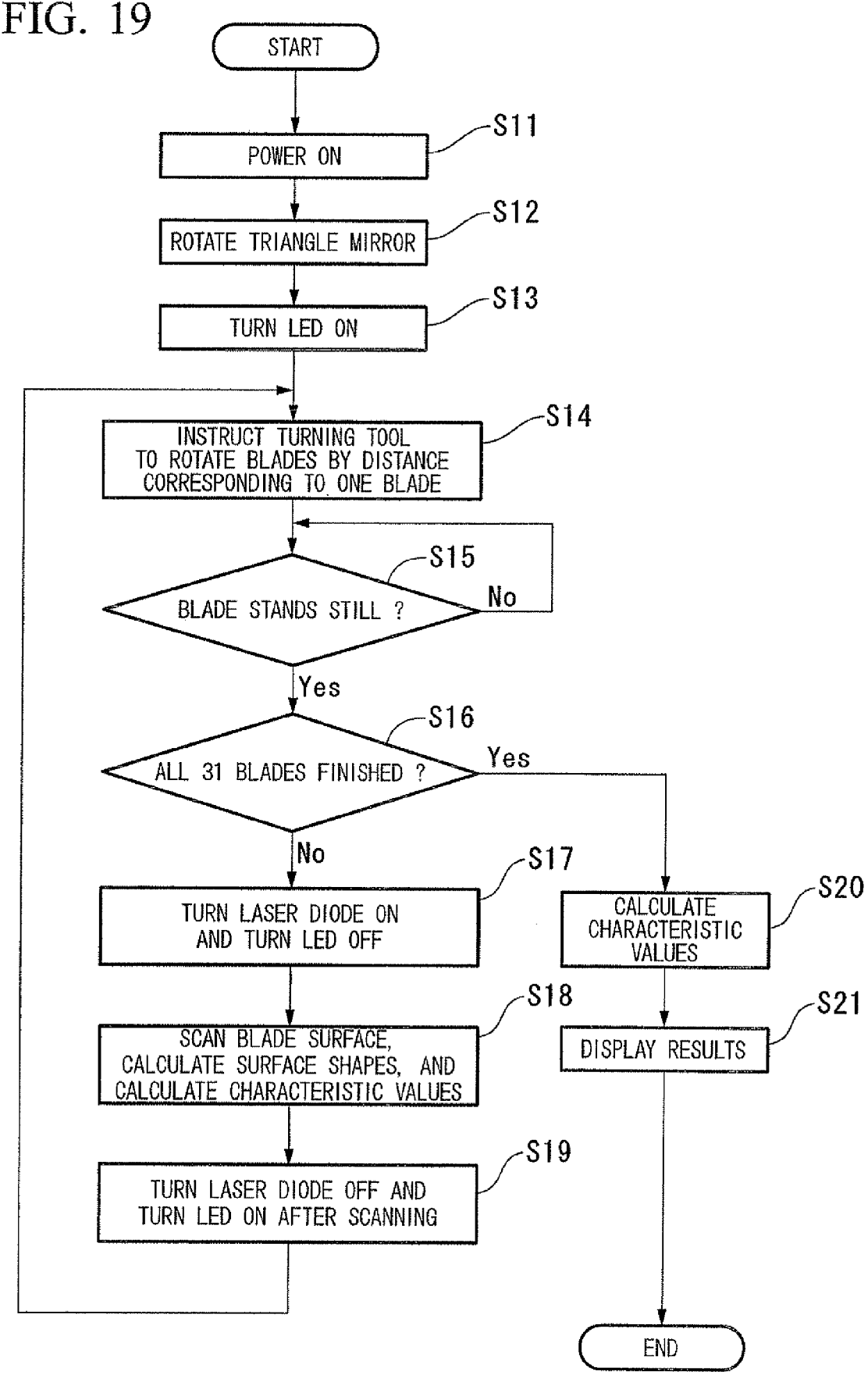
FIG. 19 is a flow chart of steps to be performed by the endoscope of FIG. 14.
Figure 20:
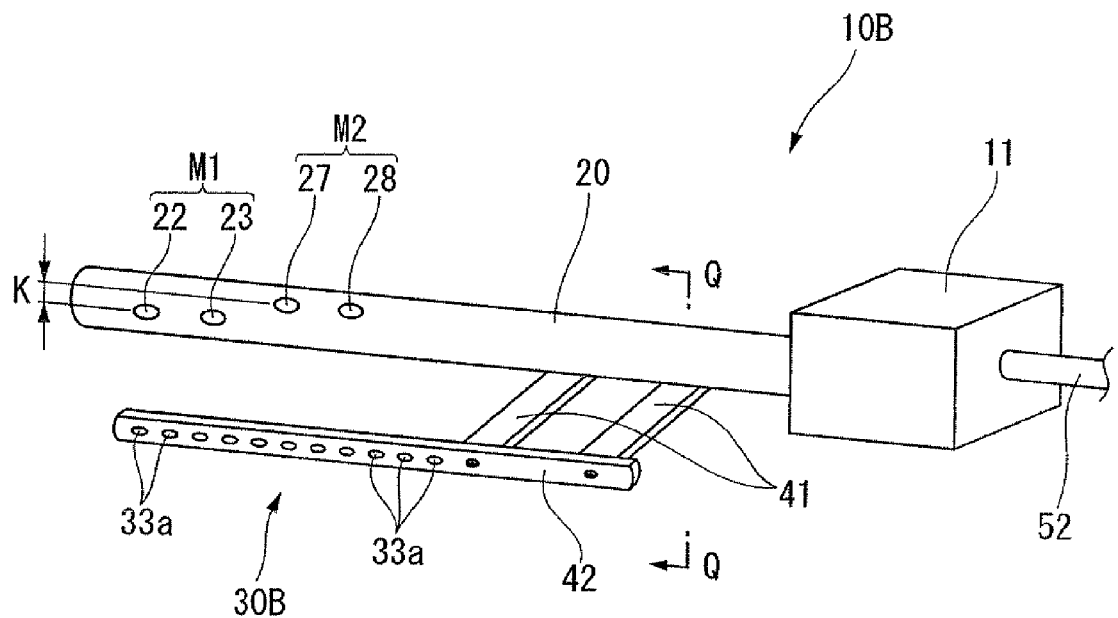
FIG. 20 is an external view showing another example of an endoscope.
Figure 21:
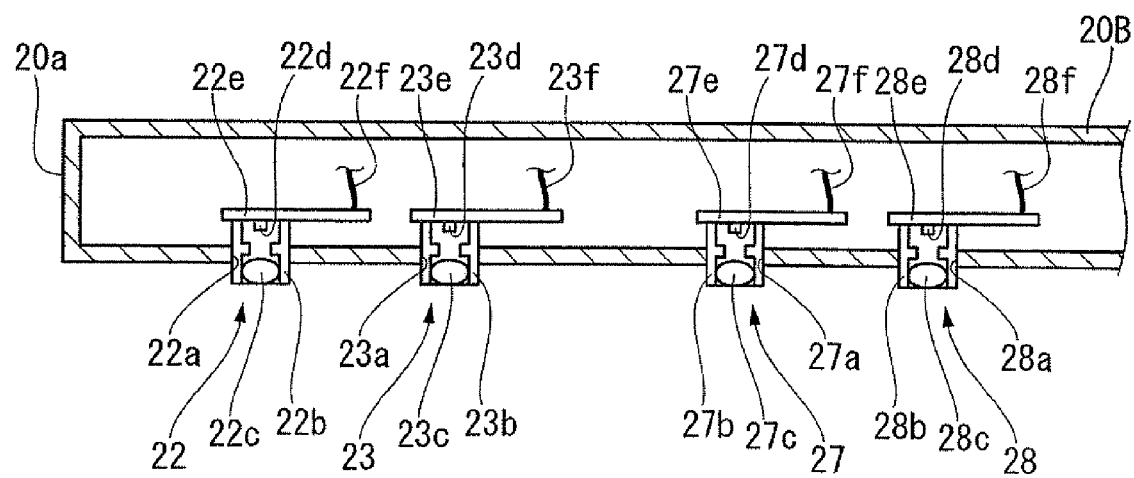
FIG. 21 is a sectional view of an insertion part of the endoscope of FIG. 20.
Figure 22A:
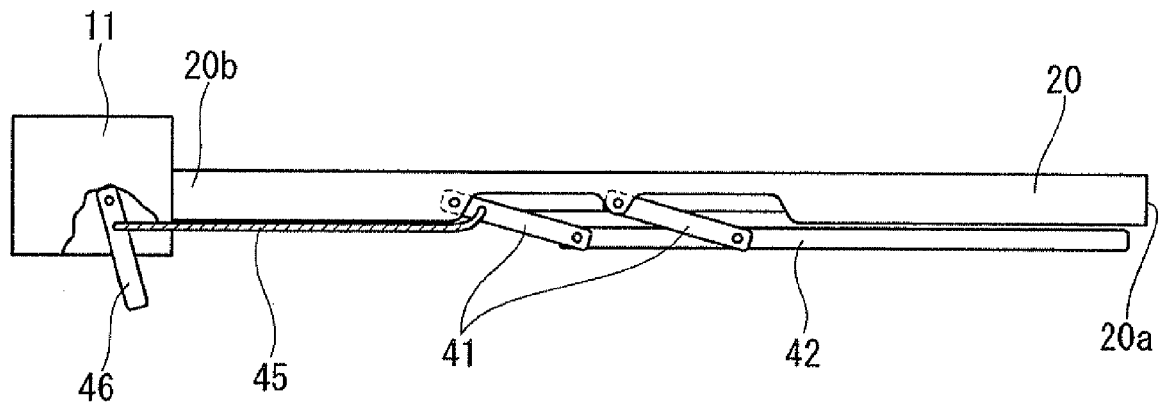
FIG. 22A is a back view of the endoscope of FIG. 20.
Figure 22B:
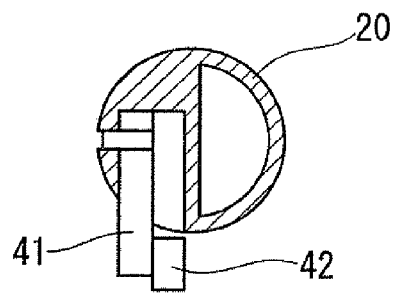
FIG. 22B is a sectional view of the endoscope of FIG. 20.
Figure 22C:
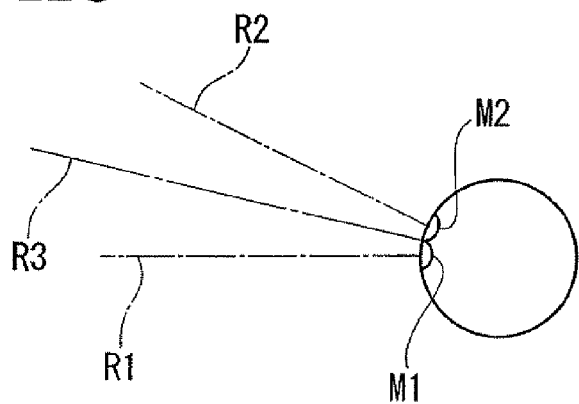
FIG. 22C is a schematic view showing an imaging direction of an imaging part.
Figure 23:
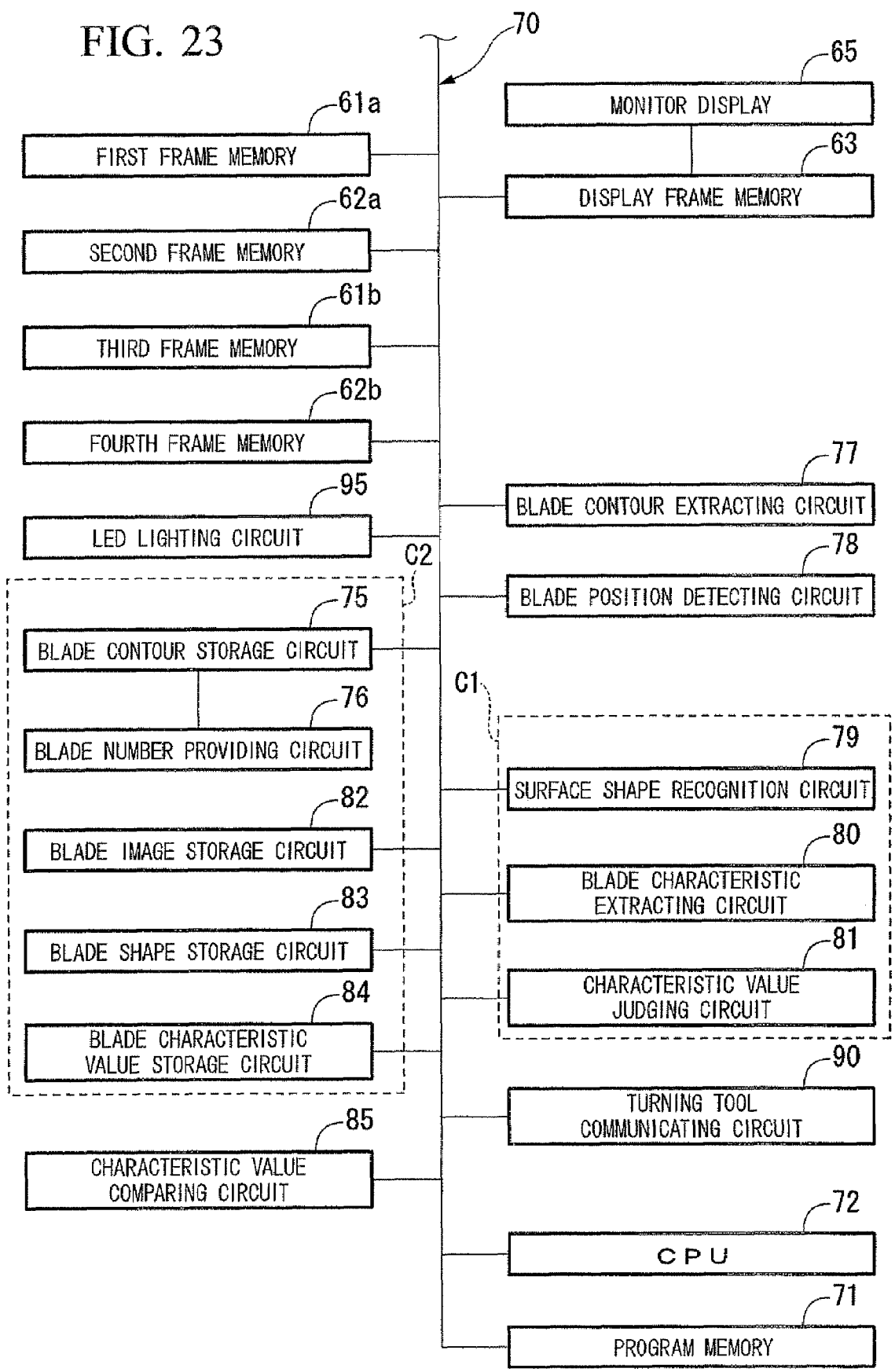
FIG. 23 is a block diagram showing the controller of FIG. 20.

FIG. 1 is an entire external view of an endoscope device.
FIG. 2 is a side view showing the details of a fixture.
FIG. 3 is an external view of an endoscope.
FIG. 4 is a sectional view of an insertion part of the endoscope of FIG. 3.
FIG. 5 is a block diagram of a controller.
FIG. 6 is a drawing showing the insertion part of the endoscope inserted in a jet engine.
FIG. 7A to FIG. 7C are drawings showing a positioning operation performed by a blade position detecting circuit.
FIG. 8A to FIG. 8D are drawings showing characteristic (damage) extraction performed by a blade characteristic extracting circuit.
FIG. 9A to FIG. 9C are drawings showing the details of the characteristic extraction of FIG. 8A to FIG. 8D.
FIG. 10A to FIG. 10C are drawings showing characteristic (coloring) extraction performed by the blade characteristic extracting circuit.
FIG. 11A and FIG. 11B are drawings showing three-dimensional shape extraction performed by a surface shape recognition circuit.
FIG. 12 is a drawing showing an example of result of the inspection.
FIG. 13 is a drawing showing an example of result of the inspection.
FIG. 14 is an external view showing another example of an endoscope.
FIG. 15 is a sectional view of an insertion part of the endoscope of FIG. 14.
FIG. 16 is a perspective view of a laser line measuring device.
FIG. 17 is a block diagram showing the controller of FIG. 14.
FIG. 18 is a display image of a blade irradiated with a laser beam.
FIG. 19 is a flowchart of the steps to be performed by the endoscope of FIG. 14.
FIG. 20 is an external view showing another example of an endoscope.
FIG. 21 is a sectional view of an insertion part of the endoscope of FIG. 20.
FIG. 22A to FIG. 22C are a back view and a sectional view of the endoscope of FIG. 20 and a schematic view showing an imaging direction of an imaging part.
FIG. 23 is a block diagram showing the controller of FIG. 20.

FIRST EMBODIMENT

The reference symbol 1 attached to FIG. 1 denotes an endoscope device according to the present invention. This endoscope device 1 includes a side viewing type hard endoscope (hereinafter, referred to as an endoscope) 10, and is used for inspecting turbine blades (corresponding to analysis areas in the present invention) installed inside a jet engine J. Although it is not particularly illustrated, the turbine blades (hereinafter, referred to as blades) H are installed so as to extend radially at appropriate intervals in a circumferential direction of a rotary shaft (not shown) to constitute a turbine.

By rotating this rotary shaft, the blades move in the circumferential direction of the rotary shaft. A turbine installed in the jet engine J is constructed by arranging 31 blades H (H1 through H31) so as to extend radially from the circumferential direction of the rotary shaft at appropriate intervals. The endoscope device 1 observes the turbine blades H by inserting the endoscope 10 into the jet engine J. An insertion part 20 of the endoscope 10 is inserted into the jet engine J from an access port 51a, which is located on the jet engine J, to capture an image of the blades H, and when the insertion part 20 of the endoscope 10 is inserted into the jet engine J, a fixture 50 detachably mounted near this access port 51a is used.

As shown in FIG. 2, the fixture 50 fixes the insertion part 20 of the endoscope 10 so as to insert the insertion part of the endoscope 10 through the access port 51a of the jet engine J, and fixing legs 52 and 53 include first links 56a and 57a rotatably fixed via pins 54a and 55a, second links 56b and 57b rotatably fixed to the tip ends of the first links 56a and 57a via link pins 54b and 55b, and presser plates 58 and 59 rotatably fixed to the tip ends of the second links 56b and 57b via pins 54c and 55c. The first links 56a and 57a and the second links 56b and 57b are provided with springs 54d and 55d which energize the links so as to draw these to each other.

The fixture 50 thus constituted is mounted by attaching the presser plates 58 and 59 on the wall face of the jet engine J. At the central portion of this fixture 50, a mount part 51b communicated with the access port 51a of the jet engine J is provided. Inside this mount part 51b, a slide cylinder (not shown) which holds the insertion part of the endoscope is fitted in a manner enabling it to be extracted.

This slide cylinder is inserted into and extracted from the mount part 51b by unillustrated rack and pinion while holding the insertion part 20 of the endoscope 10. When the insertion part 20 is inserted into the jet engine J, by an imaging part provided in the insertion part 20, the blades H inside the jet engine J are captured as an image.

On the proximal side of the insertion part 20 of the endoscope 10, a handle 11 is provided, and from this handle 11, an end of a connection cable 52 is connected. To the other end of the connection cable 52, a controller (device main body) 60 is connected. The controller 60 processes images of the blades captured by the endoscope 10, reads and displays stored images, and operates a turning tool 66. In this controller 60, a remote controller 61 and a foot switch 62 for properly operating the controller 60 are provided. In this controller 60, a monitor display 65 for displaying images captured by the endoscope 10 is provided. This controller 60 is connected with the turning tool (corresponding to the movement operating part of the present invention) 66 for rotating the blades H inside the jet engine J.

Next, the endoscope 10 will be described. As shown in the external view of FIG. 3 and the sectional view of FIG. 4, the endoscope 10 mainly includes the handle 11 and the thin and elongated insertion part 20 provided so as to extend straight outward from the tip end of the handle 11.

The insertion part 20 is a part to be inserted into the jet engine J, and on its tip end 20a side, a measuring optical system M which also serves as the observation optical system of the present invention is provided.

That is, the insertion part 20 mainly includes a cylindrical casing 21 which has a tip end closed like a bottom and is formed long and thin, a first imaging part 22 and a second imaging part 23 installed inside the cylindrical casing 21, and an illuminating part 30 installed between the first imaging part 22 and the second imaging part 23. On the outer surface of the tip end 20a side of the cylindrical casing 21, three windows arranged in the axial direction of the insertion part 20 (a first observation window 22a, an illumination window 31, and a second observation window 23a) are penetrated in line at even intervals. From the penetrated first observation window 22, illumination window 31, and second observation window 23a, the first imaging part 22, the illuminating part 30, and the second imaging part 23 are exposed to outside.

The first imaging part 22 includes a first lens frame 22b fitted in the first observation window 22a, a first objective lens 22c fitted in the first lens frame 22b, and a first observation board 22e including a first CMOS (Complementary Metal Oxide Semiconductor) image sensor 22d attached to the inner side of the first lens frame 22b. This first CMOS image sensor 22d is disposed at a focal position of the first objective lens 22c and fixed by the first observation board 22e which is fixed by the lens frame 22b. To this first observation board 22e, a first observation signal line 22f is connected, and this first observation signal line 22f is connected to the controller 60 through the inside of the connection cable 52 described above. The second imaging part 23 is constructed similarly to this first imaging part 22, so that the reference symbols (22a through 22o attached in the second imaging part 22 are attached in the drawing by replacing "22" thereof by "23," and descriptions thereof are omitted.

The illuminating part 30 is constructed so that a white LED 33 is fixed to an LED fixing frame 32 fitted in the illumination window 31. To this white LED 33, an LED power supply line 34 is connected, and is connected to the controller 60 through the inside of the connection cable 52 similarly to the above-described observation signal line 22. The insertion part 20 thus constructed is inserted into the jet engine J by the above-described fixture 50. The first imaging part 22 and the second imaging part 23 constituted as described above constitute the observation optical system of the present invention which captures the plurality of blades H for observation and also constitute the measuring optical system of the present invention which captures images of the blades for measurement.

Next, the controller 60 to which the first imaging part and the second imaging part are connected, constituting the measuring optical system, will be described. As shown in the circuit block diagram of FIG. 5, the controller 60 includes various types of memory and circuits connected by a data bus 70. These types of memory and circuits are controlled by a CPU 72 connected to the data bus 70 based on a program memory 71 connected to the data bus 70.

The various types of memories will be described. The types of memory include a first frame memory 61 to be connected to the first imaging part 22 and a second frame memory 62 to be connected to the second imaging part 23, and these frame memories 61 and 62 are connected to the data bus 70. These frame memories 61 and 62 temporarily store data (hereinafter, referred to as imaging data) captured by the first imaging part 22 and the second imaging part 23, and this stored imaging data can be transmitted to the respective circuits via the data bus 70. As other memories to be connected to the data bus 70, a display frame memory 63 to be connected to the above-descried monitor display 65 is connected to the data bus 70. This display frame memory 63 stores appropriate display data.

Next, various circuits connected to the data bus 70 to which the various memories 61, 62, and 63 are connected will be described. These various circuits mainly include a numbering circuit (corresponding to the numbering part) which numbers observation images of the respective analysis areas captured by the measuring optical system H that also serves as an observation optical system, a measuring circuit (corresponding to the measuring part) which extracts measuring information based on measuring images of the respective analysis areas captured by the measuring optical system H, a first storage circuit (corresponding to the first storage part) which stores the first analysis area information including the observation images numbered by the numbering circuit and corresponding measuring information of the analysis areas associated with the observation images extracted by the measuring circuit, a second storage circuit (corresponding to the second storage part) which stores second analysis area information including new observation images newly captured by the observation optical system and newly numbered by the numbering circuit and corresponding new measuring information of the analysis areas associated with the new observation images newly extracted by the measuring circuit, and an identifying recognition circuit (corresponding to the identifying recognition part) which identifies the first analysis area information corresponding to the second analysis area information by comparing the first analysis area information and the second analysis area information.

To the data bus 70, a turning tool communication circuit 90, which is connected to the above-described turning tool 66 and informed of appropriate information from the turning tool 66 and operates the turning tool 66, is connected. The analysis area information includes measuring information measured by the various circuits and information on the various analysis areas (blades) such as captured image data.

Next, the above-described circuits will be described in detail.

The numbering circuit is mainly constituted by a blade number providing circuit 76 which provides numbers in order. It may include a turning tool communication circuit 90. The measuring circuit is mainly constituted by the range C1 in the drawing including a surface shape recognition circuit 79. The characteristic extracting part, the characteristic value converting part, and the comprehensive characteristic value deriving part included in the measuring circuit C1 are mainly constituted by the blade characteristic extracting circuit 80. The evaluating part and the judging part of the present invention are mainly constituted by a characteristic value judging circuit 81.

Furthermore, the first storage circuit and the second storage circuit are mainly constituted by the range C2 in the drawing including a blade contour storage circuit 75, a blade image storage circuit 82, a blade shape storage circuit 83, and a blade characteristic value storage circuit 84. In this embodiment, the first storage circuit and the second storage circuit are formed by the same storage circuit in this embodiment and are constructed so as to be different from each other in the storage region inside, and the same applies to the description given below. The identifying recognition circuit is mainly constituted by a characteristic value comparing circuit 85.

Other illustrated circuits are briefly described although they are described in detail in the description on operations given below. A blade contour circuit 77 is a circuit which extracts a contour of a blade, and a blade position detecting circuit 78 is a circuit which detects whether the position of the blade is precise. A surface shape recognition circuit 79 is a circuit which mainly extracts a three-dimensional shape as a surface shape of a blade, and to the data bus 70, a LED lighting circuit 95, which controls the white LED 33 provided as the illuminating part 30, is also connected. The blade contour storage circuit 75 stores blade numbers provided by the blade number providing circuit 76 and the contours of the blades (commonly used as the observation images in the present invention) by associating these with each other.

Next, operations of the endoscope device 1 in a first embodiment constructed as described above will be described. That is, the insertion part 20 of the endoscope 10 constructed as described above is inserted into the access port 51a of the jet engine J by the fixture 50. In the fixture 50, links are arranged so as to tightly attach the presser plates 58 and 59 to the side surface of the jet engine J. The turning tool 66 is connected to a rotary shaft (not shown) that pivotally supports the blades H of the jet engine J. By using this turning tool 66, the rotary shaft pivotally supporting the blades H is rotated to move the blades H. The power supply of the controller 60 is turned on and the white LED 33 is turned on to illuminate the blade to be captured by the imaging parts 22 and 23.

For example, as shown in FIG. 6, the insertion part 20 of the endoscope 10 disposed between blades I on the fixing side (stator side) in the jet engine J captures the blade H on the movable side (rotor side) as an analysis area. In this case, by the CMOS image sensors 22d and 23d of the imaging parts 22 and 23, image signals of imaging data of the blade H are transmitted, and the image signals are temporarily stored in the first frame memory 61 and the second frame memory 62 described above. Then, necessary portions are arbitrarily cut from the image signals and transmitted to the display frame memory 63, and further transmitted to the monitor display 65 and displayed on the monitor as an observation image. In this case, the imaging parts 22 and 23 are used as an observation optical system.

On the other hand, imaging data of the first frame memory 61 is transmitted to the display frame memory 63 and the same imaging data is also transmitted to the blade contour extracting circuit 77, simultaneously. In the blade contour extracting circuit 77, based on the transmitted imaging data, a linear component and a brightness component are subjected to appropriate calculation operation to extract the contour of this blade H. The contour of the blade H extracted by the blade contour extracting circuit 77 is transmitted as measuring information for detecting the position of the blade H to the blade position detecting circuit 78.

In the blade position detecting circuit 78, the following process is performed. That is, as shown in FIG. 7A, first, two outlines are extracted with angles close to the transverse direction of the display screen G displayed based on the imaging data. Then, when the center line T1 in the horizontal direction of the display screen is set between the extracted two outlines, it is determined that one blade is within an imaging range in a desirable state, and an image signal thereof as the imaging data is transmitted to the blade contour storage circuit 75. This captured image signal is converted as a blade detection signal. When the center line T1 in the horizontal direction of the display screen is not set between the extracted two outlines, the process is maintained in a standby state in which no blade detection signal is transmitted while continuously moving the blades H by the turning tool 66 until the center line T1 in the horizontal direction of the display screen is set between the two outlines.

That is, for example, as shown in FIG. 7A, when the center line T1 in the horizontal direction of the display screen G is set between the extracted two outlines, it is determined that one blade is within the capturing range in a desirable state, and an image signal as the image data is transmitted to the blade contour storage circuit 75. Even when the center line T1 in the horizontal direction of the display screen G is set between the extracted two outlines, as shown in FIG. 7C, if a blade outline is present near the center line in the horizontal direction of the display screen, that is, when the two outlines are arranged within the range from T2 to T3 (reference symbol D) arbitrarily set, it is not determined that one blade is within the capturing range in a desirable state. As shown in FIG. 7B, depending on the blade capturing angle, a section between the blade H and its adjacent blade H is captured in an enlarged manner. Even in this case, the blade position detecting circuit 78 transmits a blade detection signal in the same manner as described above. That is, even when the outlines are plural, if the center line T1 in the horizontal direction of the display screen G is set between the plurality of outlines, it is determined that one blade is within the capturing range in a desirable state, and a blade detection signal is transmitted to the blade contour storage circuit 75.

In the blade contour storage circuit 75, every time when a blade detection signal is transmitted from the blade position detecting circuit 78, the contour of the blade H is stored based on the blade detection signal. When storing the contour of the blade H, the blade contour storage circuit 75 also stores a number (H1 to H31) of the blade H simultaneously, which is provided by the blade number storage circuit 76. Furthermore, image signals of the blade H corresponding to the outline of the blade H at the moment the blade detection signal is transmitted are also extracted from the first frame memory 61 and the second frame memory 62 and stored in the blade image storage circuit 82.

When this blade detection signal is transmitted, in the surface shape recognition circuit 79, stereoscopic measurement is performed based on the image signals of the blade H extracted from the first frame memory 61 and the second frame memory 62. This stereoscopic measurement is a method for obtaining a stereoscopic image by applying arbitrary calculation operations to the image signals of the blade H from the two imaging parts 22 and 23 as described in the above Patent document 3. A stereoscopic surface shape image obtained by this stereoscopic measurement is stored in the blade shape storage circuit 83 together with the number (H1 to H31) of the blade H provided by the blade number storage circuit 76. Thereby, the outline of the blade H and the stereoscopic image of the blade H are stored as measuring information of the blade H together with the number (H1 to H31) provided for the blade H.

Next, characteristics of the blade H to be extracted by the blade characteristic extracting circuit 80 will be described with reference to FIG. 8. The characteristics are damage characteristics mainly including cracks W1, fractures W2, dents W3, and other deformations of the blades H. The reference symbol G denotes a display image. FIG. 8A shows a contour image of a normal blade H. On the other hand, FIG. 8B shows an example in which the blade H has a crack W1. In this example, from discontinuity of the horizontal outline, it is determined that the blade H has a crack W1. In detail, as shown in the enlarged view of FIG. 9A, an absolute value of a length of the horizontal discontinuous portion is extracted as a first contour characteristic value 101, and in this discontinuous portion, an absolute value of an outline extending in the vertical direction orthogonal to the horizontal direction is extracted as a second contour characteristic value 102. A value obtained by dividing this second contour characteristic value 102 by the first contour characteristic value 101 is set as a crack characteristic value 103.

Figure 8C:
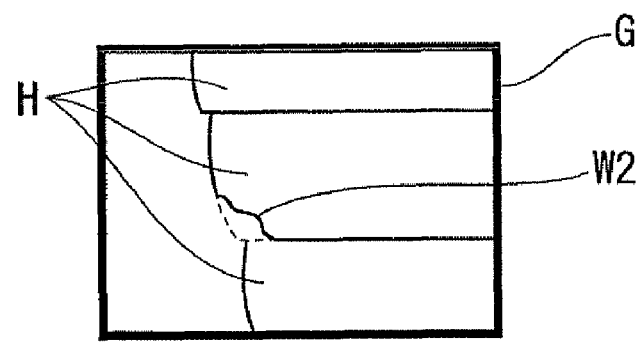
FIG. 8C is one of the drawings showing characteristic (damage) extraction performed by a blade characteristic extracting circuit.

On the other hand, FIG. 8C shows an example W2 in which a corner of the blade H is fractured. In this example, as shown in the enlarged view of FIG. 9B, when it is detected that the intersection 104 between the vertical outline and the horizontal outline is not present and two bent points 105a and 105b are present in the display screen G displayed based on image data, it is determined that this corner of the blade H has been fractured. Deviations 106a and 106b from the original intersection between the vertical outline and the horizontal outline to the bent points are set as corner fracture characteristic value 107.

Figure 8D:
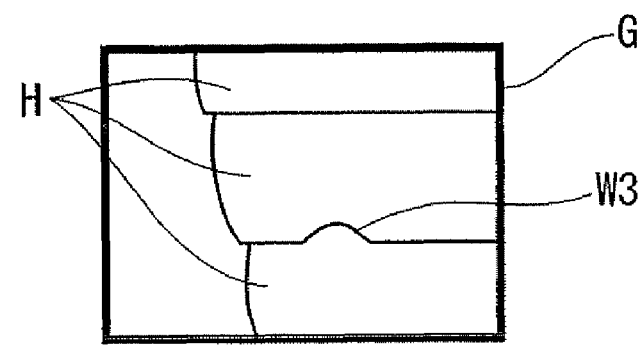
FIG. 8D is one of the drawings showing characteristic (damage) extraction performed by a blade characteristic extracting circuit.

FIG. 8D shows an example W3 in which the blade has a dent. In this example, as shown in FIG. 9C, when it is detected that the horizontal outline is discontinuous and this outline projects upward or downward vertically in the image screen G displayed based on imaging data, it is determined that something collided with this blade H and caused the dent W3. In this case, first, a depth of the dent W3 is set as a first dent characteristic value 108, and next, the distance between two intersections between a horizontal line at a position half the distance from this set first dent characteristic value 108 to the horizontal outline and the outline is set as the second dent characteristic value 109.

While the above-described characteristic values 102, 103, 107, 108, and 109 are set, image data from the first frame memory 61 and the second frame memory 62 are also transmitted to the surface shape recognition circuit 79. That is, at the time when the surface shape recognition circuit 79 receives a blade detection signal transmitted from the blade position detecting circuit 78, the surface shape recognition circuit 79 acquires image data from the first frame memory 61 and the second frame memory 62, calculates the surface shape of the blade H by means of the above-described stereoscopic measurement, and the calculated surface shape of the blade H is transmitted to and stored in the blade shape storage circuit 83.

While the characteristic values 102, 103, 107, 108, and 109 are set, in the blade characteristic extracting circuit 80, from the image data from the first frame memory 61 and the second frame memory 62, color information of the blade H is extracted as a characteristic value. That is, as shown in FIG. 10A, a distribution map of a chromaticity diagram K indicated based on the image data is set by setting the horizontal direction as an X direction and the vertical direction as a Y direction, and according to this distribution map, color information is extracted.

For example, FIG. 10A is a distribution map of a normal blade H, and as illustrated, in the blade H having no problem, the color information of each pixel is mainly distributed near the center 110. On the other hand, for example, as shown in FIG. 10B, when a portion 111 of the blade is burnt and stained burnt brown color, as shown in FIG. 10C against the burnt brown portion, the location and the burnt brown color region are extracted according to the above-described distribution map and are set as a burnt range characteristic value 112. As this color information, areas in not only the burnt brown color but also various colors are extracted and set as appropriate characteristic values. For example, an area in burnt brown color is set as 112a, an area in burnt red color is set as 112b, an area in burnt blue color is set as 112c, and a range size thereof is set as 112d.

Furthermore, in the blade characteristic extracting circuit 80, from the surface shape image data transmitted from the surface shape recognition circuit 79, the following characteristics are extracted and set. That is, as described above, based on the surface shape image data of the blade H calculated by stereoscopic measurement and stored in the blade shape storage circuit, as shown in FIG. 11A, a three-dimensional distribution map is set wherein the horizontal direction of the displayed screen is set as an X direction, the vertical direction is set as a Y direction, the depth direction is set as a Z direction (see FIG. 11B). In this case, points closest to the imaging parts 22 and 23 of the endoscope 10 are set as 0 in the Z direction.

Then, three-dimensional distribution coordinates of all points on the blade H are extracted. When all three-dimensional distribution coordinates on the blade H are extracted, an average value Zm in the Z direction of all 31 blades is extracted, and a difference dz of each blade from the average Zm is extracted. When it is determined that this difference dz exceeds a predetermined threshold Zn, the deformation of the corresponding blade H is determined as conspicuous, and dz/Zn is set as a surface deformation characteristic value 113 of the surface shape.

Image data (blade outline, blade image, and blade surface shape, etc.) and characteristic values 102, 103, 107, 108, 109, 112a, 112b, 112c, 112d, and 113 thus extracted are stored in the correspondence storage circuits 75, 82, 83, and 84 while associated with blade numbers provided by the blade number providing circuit 76. The above-described characteristic values 102, 103, 107, 108, 109, 112a, 112b, 112c, 112d, and 113 are stored in the blade characteristic value storage circuit 84. Thus, the 31 blades H are successively stored, and when the turning tool communicating circuit 90 receives a signal indicating making one revolution from the turning tool 66 meaning that the 31 blades have made one revolution, storage of all image data and characteristic values ends.

Thus, when the data of the 31 blades is stored, the stored contents are transmitted to a characteristic determining circuit 81 to perform determination of each stored characteristic values. The characteristic values to be determined by the characteristic determining circuit 81 are as shown in Table 1 below. In this characteristic determining circuit, based on the formula shown as (1), a comprehensive characteristic value is extracted, and this comprehensive characteristic value is also simultaneously stored in the blade characteristic value storage circuit 84.

TABLE 1

| Characteristic value | | Standardized coefficient | Weighting coefficient |
|---|---|---|---|
| Second contour characteristic value 102 | P1 | b1 | a1 |
| Crack characteristic value 103 | P2 | b2 | a2 |
| Corner fracture characteristic value 107 | P3 | b3 | a3 |
| First dent characteristic value 108 | P4 | b4 | a4 |
| Second dent characteristic value 109 | P5 | b5 | a5 |
| Burnt brown color area 112a on blade surface | P6 | b6 | a6 |
| Burnt red color area 112b on blade surface | P7 | b7 | a7 |
| Burnt blue color area 112c on blade surface | P8 | b8 | a8 |
| Burnt range size 112d | P9 | b9 | a9 |
| Surface deformation value 113 | P10 | b10 | a10 |

$$\text{Comprehensive characteristic value} = \sum_{i=1}^{10} Pi \times bi \times ai \quad (1)$$

As described in Table 1, to each of the characteristic values, predetermined standardized coefficients (b1 to b10) are provided. Thereby, each characteristic value can be compared with other characteristic values by the same scale. As described in Table 1, to each of the characteristic values, weighing coefficients (a1 to a10) using predetermined evaluation functions are provided. By summing the characteristic values by the functions of the formula (1) using the standardized coefficients (b1 to b10) and the weighing coefficients (a1 to a10), a comprehensive characteristic value obtained by summing the characteristic values of the blade H can be preferably derived.

These weighing coefficients (a1 to a10) successively weigh the damage characteristic values in order from the most important to the least important, so that a damage characteristic which is slight in degree as a blade H is not greatly reflected on the comprehensive characteristic value, and damage characteristic values that are fatal upon a blade H are greatly reflected on the comprehensive characteristic value. For example, in general, the crack W1 expands more rapidly than the dent W3. If this crack W1 expands, the corresponding blade becomes useless as a blade. Therefore, the weighing coefficients (a2) of the crack characteristic value 103 are selected twice the value of the weighting coefficients of the dent characteristic values 108 and 109. Thereby, when extracting a comprehensive characteristic value, the crack characteristic value 103 is weighed twice as much as the dent characteristic values 108 and 109 so as to be greatly reflected on the comprehensive characteristic value.

Herein, it is also possible that when the characteristic values 102, 103, 107, 108, 109, 112a, 112b, 112c, 112d, or 113 exceeds a predetermined threshold, the blade H having the characteristic value exceeding the threshold is marked or when a comprehensive characteristic value derived as described above exceeds a predetermined threshold, the blade having this comprehensive characteristic value exceeding the threshold is marked, and then stored together with a blade number in each storage circuit 75, 82, 83, and 84. When the characteristic values 102, 103, 107, 108, 109, 112a, 112b, 112c, 112d, or 113 exceed a predetermined threshold, this means that the corresponding damage is conspicuous.

When the above-described series of operations are ended, based on storage stored in the storage circuits 75, 82, 83, and 84, for example, the result of inspection as shown in FIG. 12 are displayed on the monitor display 65. This result of inspection is displayed so that the entire image corresponding to the number of blades H is displayed and an image of a portion and a blade with regard to the characteristic value exceeding a threshold as described above can be selected.

Next, a characteristic value comparing circuit 85 which compares the characteristic values will be described. In this characteristic value comparing circuit 85, any arbitrarily selected one of the characteristic values 102, 103, 107, 108, 109, 112a, 112b, 112c, 112d, and 113 of the blades previously stored in the storage circuits 75, 82, 83, and 84 and newly acquired and stored characteristic values corresponding to the arbitrarily selected characteristic value of the blades H are compared with each other. That is, to associate newly acquired and stored characteristic values of the blades with the previously stored characteristic values of the blades, it is necessary to identify blades corresponding to the blade numbers of the previous blades. That is, every time when the blade H is observed, it is unknown which new blade corresponds to the number of the previous blade H, so that the new blade corresponding to the previous number must be identified.

Therefore, in detail, as shown in Table 2 below, a list of values of an arbitrarily selected characteristic of the blades H which were previously stored and a list of values of the arbitrarily selected characteristic of the blades H which were newly stored are compared with each other, at a point at which the number of matching points of the arbitrarily selected characteristics value is maximized, the previous blade numbers (H1 to H31) are identified, and the new arbitrarily selected characteristic values of the current blades (H1 to H31) are stored by being associated with the identified blade numbers (H1 to H31). When the new arbitrarily selected characteristic values are stored by being thus associated, as shown in FIG. 13, on the monitor display 65, the previous images and the current images are displayed by rearranging orders for easy comparison. When the previous images and the current images are thus rearranged and displayed, an operator can preferably notice a change in the state over time for the same blade.

TABLE 2

(a)

| | Characteristic value | 0 | 3 | 0 | 0 | 8 | 0 | 0 | ... | 0 |
|---|---|---|---|---|---|---|---|---|---|---|
| Previous | Blade | $H_1$ | $H_2$ | $H_3$ | $H_4$ | $H_5$ | $H_6$ | $H_7$ | ... | $H_{31}$ |

(b)

| | Characteristic value | 0 | 0 | 0 | 3 | 0 | 1 | 9 | ... | 2 |
|---|---|---|---|---|---|---|---|---|---|---|
| Current | Blade | $H_1$ | $H_2$ | $H_3$ | $H_4$ | $H_5$ | $H_6$ | $H_7$ | ... | $H_{31}$ |

(c)

| | Characteristic value | 0 | 3 | 0 | 1 | 9 | 0 | 0 | ... | 0 |
|---|---|---|---|---|---|---|---|---|---|---|
| Current | Blade | $H_3$ | $H_4$ | $H_5$ | $H_6$ | $H_7$ | $H_8$ | $H_9$ | ... | $H_2$ |

In the above-described characteristic value comparing circuit 85, any arbitrarily selected one of the characteristic values 102, 103, 107, 108, 109, 112a, 112b, 112c, 112d, and 113 of the blade H previously stored in the storage circuits 75, 82, 83, and 84 and a newly acquired and stored characteristic value of the blade H corresponding to the arbitrarily selected one are compared with each other, however, without limiting to this, the arbitrarily selected characteristic value may be plural, or may be the comprehensive characteristic value.

The above-described series of steps are performed based on programs set for each circuit; however, it is also possible that the steps are performed by the CPU 72 based on a program connected to the data bus 70 and stored in the program memory 71. With regard to moving the blades H, instead of using the turning tool 66, the blades H may be moved by manual operations by an operator. In this case, it is enough that the controller 60 is informed of only the start of measurement. In addition to the above-described circuit, even when arbitrary circuits are provided; it is not a deviation from the spirit of the present invention.

As described above, in this endoscope device, by the characteristic value comparing circuit (identifying recognition part) 85, information (including observation images) including characteristic values measured by the various circuits as the previous (first) information of the blades H and information including characteristic values measured by the various circuits as the current (second) information of the blades H are compared to identify the previous information of the blades H corresponding to the current information of the blades H, and the newly acquired current information of the blades H are stored in the storage circuits 75, 82, 83, and 84, so that the comparison between the previous information of the blades H and the current information of the blades H becomes easy. Thereby, changes in the state of the blades H can be preferably noticed. The blades H are also provided with numbers (numbered), so that it is also possible to immediately read the noticed change in the state of the blade H which an operator desired to observe in detail from the storage circuits 75, 82, 83, and 84. That is, changes in the state of the plurality of blades H can be noticed at one time, and furthermore, the blades H can be accurately inspected one by one, so that automation (labor saving) of the process is realized and the difficulty in the inspection can be eliminated.

In this endoscope device 1, the measuring optical system also serves as an observation optical system, so that it becomes unnecessary to newly provide an observation optical system for imaging to observe the blades H and the number of parts can be reduced, and the insertion part 20 can be made compact. This endoscope device 1 includes a movement operating part which successively moves the blades H so that the blades H are captured by the observation optical system and the measuring optical system, and when the movement operating part moves one of the plurality of the blades H and when the movement operating part moves the plurality of blades H so that the plurality of blades make one revolution, the movement operating part informs the measuring circuit C1 or the blade number providing circuit 76 of this, so that it is not necessary both to independently count the movements of the blades H one by one or to confirm the revolution of the blades H. Thereby, the control can be simplified.

In this endoscope device 1, when comparing previous characteristic values of the blade H with new characteristic values, the multiple kinds of characteristics can be compared with each other in time series, so that changes in the state of the blade H can be easily noticed. In this endoscope device 1, the multiple kinds of characteristics to be extracted by the measuring circuit C1 are cracks, fractures, dents, and damages including other deformations of the blades H, so that the damage conditions of the blades H can be easily noticed and replacement timing of the blades H can be preferably noticed.

In this endoscope device 1, multiple kinds of characteristic values are subjected to standard quantification, so that the multiple kinds of characteristic values can be compared with each other by the same scale. When the characteristics are thus quantified, the degrees of the characteristics can be determined by the numerical values, and the characteristics can be easily determined. In this endoscope device 1, comprehensive damage values can be derived to the measuring circuit C1, so that by comparing comprehensive damage characteristic values, damage as one blade can be determined. When comprehensive characteristics are thus quantified, the degrees of the characteristics can be determined by the numerical values, and the damage characteristics can be easily determined.

The characteristic value determining circuit 81 may be constituted so as to provide appropriate evaluation to each blade based on the derived characteristic values according to, for example, a five grade system. Based on the evaluations, according to whether the threshold is exceeded, the blades H are determined as conforming or nonconforming. When evaluation and determination are thus performed, without determination by a skilled operator, the replacement timings of the blades H are instantaneously known.

SECOND EMBODIMENT

Next, a second embodiment different from the above-described first embodiment will be described. The endoscope device in this second embodiment and the endoscope device in the first embodiment are different from each other in the constitution of image measurement for stereoscopic capturing. That is, in the endoscope 10 of the first embodiment, when stereoscopically capturing the blades H, a stereoscopic measuring method is used, however, in the endoscope 10A of the second embodiment, for stereoscopic capturing, a laser line measuring method (light-section method) is used. Components constituted in the same manner as in the endoscope device of the first embodiment are attached with the same symbols, and descriptions thereof are omitted. In the first imaging part 22 of the endoscope device of this second embodiment, instead of the CMOS image sensor 22d (see FIG. 5), a CCD (Charge Coupled Devices) image sensor 22g is provided.

That is, at a portion of the second imaging part of the endoscope device of the first embodiment, instead of the imaging part 23 constituted as described above, a laser line measuring mechanism 24 is provided. As shown in the external view of FIG. 14 and the sectional view of FIG. 15, to the second observation window 24a of the first embodiment, a projecting window frame 24b is attached, and in the insertion part 20A near this projecting window frame 24b, a laser line measuring device 25 which irradiates the blades H with light through this observation window 24a is provided. This laser line measuring device 25 mainly includes, as shown in FIG. 16, a triangle mirror 25a rotatably and pivotally supported, a motor 25b for rotating this triangle mirror 25a, a laser diode 25c for irradiating this triangle mirror 25a, and a cylindrical lens 25d disposed between the laser diode 25c and the triangle mirror 25a. This laser diode 25c is connected to the laser diode lighting circuit 67 of the controller 60 by an arbitrary electric wire 67a.

To the rotary shaft of the motor 25b, a pulley 25e is attached, and a pulley 25f is attached to a rotary shaft as well which pivotally supports the triangle mirror 25a, and around these pulleys 25e and 25f, an endless timing belt 25g is wound so as to interlock the pulleys 25e and 25f with each other. To the rotary shaft of the pulley 25f pivotally supporting the triangle mirror 25a, an arbitrary encoder 25h is provided, and in this projection window frame 24b, an arbitrary slit (not shown) is formed. This encoder is connected to an encoder input circuit 68 of the controller 60 by an arbitrary electric wire 68a.

According to the laser line measuring mechanism 25 thus constituted, as shown in FIG. 16, a laser beam L emitted from the laser diode 25c is transmitted through the cylindrical lens 25d and made incident on the triangle mirror 25a, and the laser beam L that has been made incident on the triangle mirror 25a is reflected by the triangle mirror 25a. Thereby, the laser beam shines out from the second observation window 24a toward the blades H. Furthermore, according to the rotation of the triangle mirror 25a, the laser beam is transmitted through the slit formed in the projection window frame 24b, whereby the laser beam (linear in the vertical direction) La shining out from the laser line measuring mechanism 25 moves while slidingly irradiating the blades H. At this time, the first imaging part 22 captures the laser beam moving on the blades H. FIG. 18 is a display image on the monitor display 65 when the laser beam is irradiated.

The laser beam L that thus slidingly irradiates the blades H is captured by the first imaging part 22, and imaging data thus obtained is transmitted to the controller 60. This laser line measuring mechanism 25 is connected to the laser diode lighting circuit 67 and the encoder input circuit 68 connected to the data bus 70 inside the controller 60 as shown in the block diagram of FIG. 17 to supply arbitrary power and perform arbitrary inputting.

Operations of the endoscope device of the second embodiment constituted as described above will be described with reference to the flowchart of FIG. 19. In the description given below, only different operations as a result of employment of a constitution different from that of the endoscope device of the first embodiment described above will be described, and description of the same operations as those of the endoscope device of the first embodiment will be omitted.

That is, when the controller 60 is turned on (S11), the encoder input circuit 68 is turned on and rotates the rotary shaft of the motor 25b, and accordingly, the triangle mirror 25a which is interlocked with the motor 25b rotates (S12). Simultaneously, the LED is turned on by the LED lighting circuit 95 (S13). The CPU 72 controls the turning tool 66 via the turning tool communicating circuit 90 to move one blade so as to measure next one blade H.

At this time, when the blade position detecting circuit 78 does not confirm that the moved blade H is standing still, the CPU 72 connected to the data bus 70 turns the LED lighting circuit 95 on, and furthermore, turns the laser diode lighting circuit 67 off. Until the blade H, which is moved by the turning tool 66, stands still, the laser diode 25c is off, and the white LED 33 is on and illuminates the blade H (S15).

When the blade position detecting circuit 78 has confirmed that the blade H is standing still (S15), it is determined whether the calculation of three-dimensional shapes of all 31 blades (H1 to H31) is finished (S16). At this point, when it is determined that the scanning of all 31 blades (H1 to H31) is not finished, the CPU 72 turns the white LED 33 off and turns the laser diode 25c on (S17). Then, the CPU 72 rotates the triangle mirror 25a.

According to this rotation of the triangle mirror 25a, the laser beam (linear in the vertical direction) which is output by transmitting through the projection window frame 24b moves while irradiating the blade H, and at the same time, the first imaging part 22 captures the laser beam La moving on this blade H. That is, the blade H is scanned.

Then, the surface shape recognition circuit 79, based on the images of the blades H which are line-sectioned and captured by the first imaging part 22, applies arbitrary calculation operations (based on a triangulation method) to the position of the captured line and arbitrary information of the encoder input circuit 68 (S18). Thereby, a three-dimensional surface shape of the blade H is calculated. Then, when the calculation of the three-dimensional surface shape of the blade H is finished (completely scanned), the CPU 72 turns the laser diode 25c off and turns the white LED 33 on (S19). This series of steps (S14 to S16) are repeated until scanning of all 31 blades (H1 to H31) is finished. At S16 described above, when the calculation of the three-dimensional surface shapes of all 31 blades is finished, comprehensive characteristic values or the like are calculated (S20), and the results of calculation are displayed on the monitor display part 65 and the process ends (S21).

In other words, until capturing by the first imaging part 22 is completed, the turning tool 66 is controlled via the turning tool communicating circuit 90 to prevent the movement of the 31 blades, that is, prevent rotation of the rotary shaft to which the blades H are attached.

In other words, every time the blades H are moved by a distance corresponding to one blade by the turning tool 66, the blades H is confirmed whether they are standing still or not by the blade position detecting circuit 78, and thereafter, a surface shape of the blade H is scanned by the laser line measuring mechanism 25. When the blades are moved by a distance of one blade or the set of 31 blades are moved (make one revolution), the turning tool informs the blade position detecting circuit of this.

By this stereoscopic (three-dimensional) capturing, the depth of the blade can be easily measured in addition to the longitudinal length and the transverse length of the blade, and characteristics thereof can be more preferably noticed. In addition, a laser line measuring method (light-section method) is used, so that the manufacturing cost can be reduced.

THIRD EMBODIMENT

Next, a third embodiment different from the first embodiment and the second embodiment described above will be described. The endoscope device 10B in this third embodiment is different from the first embodiment in that two sets of the optical system M including the first imaging part and the second imaging part of the endoscope device 10 described in the first embodiment are provided in the longitudinal direction of the insertion part 20. The endoscope device 10B in this third embodiment is different from that of the first embodiment in that the illuminating part 30 of the endoscope device 10 described in the first embodiment is provided in an elongated member 42 which is provided so as to extend in parallel in an axial direction of the insertion part 20 and move toward and away from the insertion part 20 via a link member 41.

The components constituted similarly to those of the endoscope device 10 of the first embodiment are attached with the same reference symbols and description thereof will be omitted. The additional set of the optical system M includes imaging parts 27 and 28, and description thereof is omitted by replacing "22" of the reference symbols (22a through 22f) attached in the second imaging part 22 with "27" and "28" and using the replaced numbers in the drawing. The first imaging part 22 of the first optical system M1 is connected to the first frame memory 61a, the second imaging part 23 of the first optical system M1 is connected to the second frame memory 62a, the first imaging part 27 of the second optical system M2 is connected to the third frame memory 61b, and the second imaging part 28 of the second optical system M2 is connected to the fourth frame memory 62b (see FIG. 23). Images captured by the first optical system M1 and the second optical system M2 are pieced together so as to form an image of the whole of the blade H.

In detail, as shown in the external view of FIG. 20 and the sectional view of FIG. 21, the insertion part 20 of the endoscope 20B includes one set of optical systems (first optical system set) M1 including the first imaging part 22 and the second imaging part 23 which are provided in the insertion part 20 of the endoscope 10 of the first embodiment described above, and another optical system (second optical system set) M2 including the third imaging part 27 and the fourth imaging part 28, provided on proximal side of the one set of the optical system.

The first optical system set M1 and the second optical system set M2 are provided by being shifted from each other along the circumferential direction of the outer peripheral surface of the insertion part 20 in which they are installed. That is, as shown in FIG. 20, the second optical set M2 is shifted to an upper side by an angle of about 20 degrees in the circumferential direction of the insertion part 20 than the first optical system M.

That is, a deviation K is given between the optical systems M1 and M2 as illustrated. In other words, as shown in the schematic view of FIG. 22C, a capturing central direction of the optical system M1 is indicated as R1, and a capturing central direction of the optical system M2 is indicated as R2. When performing capturing by these first optical system M1 and second optical system M2, the center of the blade H to be captured is moved to the central direction R3 which is located between the first optical system M1 and the second optical system M2.

Furthermore, in the insertion part 20 of the endoscope device 10B of the third embodiment, two link members 41 are rotatably and pivotally supported. Ends of the link members 41 are rotatably and pivotally supported on the insertion part 20, and the other ends rotatably and pivotally support the elongated member 42. The elongated member 42 pivotally supported by the link members 41 is constituted so as to extend in parallel in the axial direction of the insertion part 20, and becomes capable of moving toward and away from the insertion part 20 by being pivotally supported by the link members 41. In the above-described elongated member 42, a plurality of white LEDs 33a for illuminating the blade H are arranged in line along the longitudinal direction. These white LEDs 33a are connected to the LED circuit 95 (see FIG. 23).

As shown in FIG. 22A which is a view of FIG. 20 from the back side and FIG. 22B which is a sectional view along Q-Q of FIG. 20, to the ends of the link members 41 pivotally supported on the insertion part 20, one end of an operating shaft 45 is connected at a side further inward than the points where the link members are pivotally supported on the insertion portion 20. The other end of the operating shaft 45 is connected to the operating lever 46 which is pivotally supported by the handle part 11. Thereby, according to a rotational operation of an operation lever 46, the operating shaft 45 can be pushed toward the distal end 20a side of the insertion part 20 and pulled toward the proximal end side 20b of the insertion part 20. Thereby, the link members 41 connected to the operating shaft 45 are raised from or moved down to the insertion part 20. Thereby, the elongated member 42 connected to the link members 41 is moved toward and away from the insertion part 20 while maintained to be in parallel to the insertion part 20.

The endoscope device 10B of the third embodiment thus constituted provides the following effects. That is, two sets of optical systems M are provided, so that capturing on a wide range is possible. For example, even when a blade or the like which is too large to be preferably captured by one set of optical systems is desired to be captured, without dividing the range of this large blade H, the blade H can be captured at one time. Furthermore, conventionally, when attempting to capture such a large blade H at one time, a wide-angle lens is used, however, when capturing is performed by using such a wide-angle lens, the resolution of a captured image is low, and when the blade is measured by the measuring circuit C1 based on the captured image, the measurement accuracy becomes low. However, as in the case of the endoscope device 10B of this third embodiment, when two sets of optical systems are provided, the resolution of the captured images can be increased, so that the blade H can be captured with high accuracy.

In addition, the white LEDs 33 are provided in the elongated member 42, so that a problem in which intensive light that has struck the blade H becomes difficult to enter the imaging parts 22, 23, 27, and 28 and blurred images in white (halation) hardly occur, so that observation and measurement of the blade H can be preferably performed. Furthermore, the illuminating part 30B is arranged in the longitudinal direction of the elongated member, so that even when the blade H is constituted long, the whole of the blade H can be illuminated.

The endoscope device according to the present invention is not limited to the above-described embodiments, and can be selectively constituted arbitrarily within a range with no deviation from the spirit of the present invention.

For example, the emitting part of the above-described embodiments is constituted by an LED, however, the present invention is not limited to this, and it may be constituted by an arbitrary light source such as a lamp or a light guide or the like. The endoscope device of the present invention may be provided with three or more sets of the above-described optical system M1 (M2).

In the above-described embodiments, when imaging a blade as an analysis area, it is captured while illuminated by the illuminating part. However, it is also possible that the illuminating part is turned on like a photoflash in timing, at which the position of the blade is detected, to illuminate and capture the analysis area. In the case where the illuminating part is thus turned on like a photoflash, there is an advantage that a still image with reduced blur can be preferably captured.

It is also possible that, instead of the illuminating part of the above-described embodiments, a random pattern is projected so as to make matching of stereoscopic measurement easier.

In this endoscope device, the identifying recognition part identifies the first analysis area information corresponding to the second analysis area information by comparing the first analysis area information and the second analysis area information, and when the second storage part newly stores second analysis area information, the first storage part stores second analysis area information corresponding to the first analysis area information identified by the identifying recognition part in addition to the first analysis area information, and this makes easier the comparison between the previous first analysis area information and the updated second analysis area information. Thereby, changes in the state of the analysis areas can be preferably noticed. Furthermore, due to numbering by the numbering part, noticed changes in the state of the analysis area can be read from the storage parts immediately. That is, changes in the state of the analysis area can be noticed at one time, and furthermore, the analysis area can be accurately inspected respectively, so that automation of the process (labor saving) is realized and the difficulty in the inspection can be eliminated.

In this endoscope device, the measuring optical system also serves as an observation optical system, so that it becomes unnecessary to provide a new observation optical system for capturing the analysis areas for observation and the number of parts can be reduced. Thus, the insertion part can be made compact. No observation optical system is additionally provided, and this leads to a reduction in manufacturing cost.

This endoscope device includes a movement operating part which successively moves analysis areas so that the analysis areas are captured by the observation optical system and the measuring optical system, and the movement operating part is constituted so that, when it moves one of a plurality of the analysis areas and when it moves the plurality of analysis areas so that the plurality of the analysis areas makes one revolution, the movement operating part informs the measuring part or numbering part of this, so that the analysis areas can be moved at the measuring part so they are preferably captured. With regard to the numbering parts, images of the individual analysis areas can be quickly numbered without counting movements of the analysis areas one by one and without confirming the plurality of the analysis areas to make one revolution.

In the measuring part of this endoscope device, a characteristic extracting part which extracts multiple kinds of characteristics from the measuring information is provided, and the first storage part and the second storage part store the multiple kinds of characteristics as part of the measuring information, so that in comparison between the previous measuring information and the updated measuring information of the analysis areas, multiple kinds of characteristics can be compared in time series, and this makes easier to notice changes in the state of the analysis areas.

In this endoscope device, multiple kinds of characteristics to be extracted by the characteristic extracting part are cracks, fractures, dents, and damages including other deformations of the analysis areas, and this makes easier to notice the damaged conditions of the analysis areas and also makes preferable to notice replacement timing of the analysis areas.

In the measuring part of this endoscope device, a characteristic value converting part is provided which converts the multiple kinds of characteristics into multiple kinds of characteristic values, which was normally quantified by a predetermined evaluating calculation, and the first storage part and the second storage part store the multiple kinds of characteristic values as a part of the measuring information, so that when comparing the previous measuring information with the updated measuring information of the analysis area, the multiple kinds of characteristic values, which are normally quantified, are only compared. This quantification of the characteristics makes it possible to determine the value of the characteristics by the amount of the numerical values, so that the characteristics can be easily determined.

The standard quantification means quantification of the multiple kinds of characteristics so that they are easily compared, and according to the standard quantification, various characteristics can be determined by the same scale, and makes easier to notice changes in the state of the analysis areas and accordingly makes preferable to determine the analysis areas.

In the measuring part of this endoscope device, a comprehensive characteristic value deriving part is provided which drives a comprehensive characteristic value of an analysis area by weighting and summing up the multiple kinds of characteristic values, and the first storage part and the second storage part store the multiple kinds of the comprehensive characteristic values as a part of the measuring information, so that even if each of the various characteristics are small or the characteristics are great as a whole, the characteristics as a whole can be determined by comparing the comprehensive characteristic values. By thus quantifying the comprehensive characteristics as described above, the amount of the characteristics can be determined by the numerical values, and the characteristics can be easily determined. Therefore, a comprehensive (whole) characteristic of each analysis area can be determined, and a change in the state of the analysis area can be easily noticed and the analysis area can be preferably determined.

In this endoscope device, changes in the state of analysis areas which become easier to be noticed can be evaluated by the evaluating part, so that it becomes easy to determine whether the analysis areas are conforming or nonconforming.

In this endoscope device, the judging part which determines whether the analysis areas are conforming or nonconforming based on the evaluation made by the evaluating part is provided, so that from the determination whether the analysis areas are conforming or nonconforming made by the judging part, replacement timing of the analysis areas are instantaneously known without the operator's judgment.

In this endoscope device, the measuring optical system has two or more imaging parts whose installation positions are shifted from each other to stereoscopically image an analysis area so that when measuring an image of the analysis area by the measuring part, a three-dimensional image of the analysis area can be measured. Thereby, the depth of this analysis area can also be measured as well as the longitudinal length and transverse length. That is, the analysis area can be three-dimensionally measured, and the characteristics thereof can be more preferably noticed.

In this endoscope device, the measuring optical system has an imaging part which captures an analysis area by the light-section method, and stereoscopically captures the analysis area, so that although only one imaging part is provided, when measuring an image of an analysis area by the measuring part, a three-dimensional image of the analysis area can be measured. Thereby, the depth of the analysis area can also be measured as well as the longitudinal length and the transverse length, the analysis area can be three-dimensionally measured, and the characteristics of the analysis area can be more preferably noticed.

In the insertion part of this endoscope device, an illuminating part which illuminates the analysis area is provided, so that it becomes unnecessary to separately provide illuminating means for illuminating the analysis area, and the whole of the endoscope device can be made compact. This action is particularly advantageous when a region for inserting the endoscope into the area to be analyzed is especially narrow. It is unnecessary to separately provide an illuminating means, so that the manufacturing cost can also be reduced.

In the insertion part of this endoscope device, an elongated member which extends in parallel in an axial direction of the insertion part and is movable toward and away from the insertion part via a link member is provided. In the elongated member, an illuminating part which illuminates an analysis area is arranged in line in a longitudinal direction, so that the illuminating part can move forward and away from the insertion part so as to properly adjust the light intensity for illuminating the analysis area. The illuminating part is provided in the elongated member separated from the insertion part provided with the observation optical system and the measuring optical system, so that light for inspection enters the observation optical system and the measuring optical system at an arbitrary angle of inclination. Then, an intensive light hardly enters, thereby a problem in which the analysis area (halation) blurred hardly occurs, and the analysis area is preferably observed and measured. Furthermore, the illuminating part is arranged in parallel in the longitudinal direction of the elongated member, so that even when the area to be analyzed is long, the whole of the analysis area can be illuminated.

In this endoscope device, two or more sets of the measuring optical systems are provided in the longitudinal direction of the insertion part, so that even when the area to be analyzed is long, the whole of this analysis area can be observed (measured) at one time, and so that the difficulty in observation (measurement) of an analysis area by dividing can be eliminated.

In this endoscope device, the sets of the measuring optical systems are provided by being shifted from each other in the circumferential direction of the insertion part, so that a range to be observed (measured) of an analysis area can be expanded in the circumferential direction of the insertion part. Thereby, the problem in observation (measurement) of the analysis area by dividing the analysis area can be solved.

According to the endoscope device of the present invention, when inspecting turbine blades of jet engines, automation (labor saving) of this inspection process is realized by reducing the number of steps of the inspection, and the difficulty in the analysis area inspection can be eliminated.

What is claimed is:
1. An endoscope device comprising:
   an image capture portion that captures an image of a blade provided in an engine; and
   a position detection portion embodied in a machine, the position detecting portion being configured to:
   calculate a brightness component of image data associated with the image captured by the image capture portion; and
   determine whether or not the blade is at a position that enables the blade to be image captured at least based upon the brightness component of the image data, the brightness component resulting from the machine's analysis of the image data.

2. The endoscope device according to claim 1, further comprising:
   a display portion that displays the image, wherein
   the position detection portion determines whether or not the blade is at a position that enables the blade to be image captured by extracting two outlines with angles close to the transverse direction of the display portion displayed based on the image captured by the image capture portion.

3. The endoscope device according to claim 2, wherein the position detection portion determines the blade to be at the position that enables the blade to be image captured when a center line in the horizontal direction of the display portion is set between the extracted two outlines.

4. The endoscope device according to claim 2, wherein the position detection portion determines the blade to be positioned in the position that enables the blade to be image captured, even when there are more than two outlines, if the center line in the horizontal direction of the display portion is set between the outlines.

5. The endoscope device according to claim 1, further comprising:
   a measuring portion that measures a characteristic value of the blade based on the image when the blade is determined to be at a position that enables the blade to be image captured by using the image captured by the image capture portion, and
   a recording portion that records the characteristic value and the image used for measuring the characteristic value.

6. The endoscope device according to claim 5, further comprising:
   a numbering portion that provides the image with a number, wherein
   the recording portion records the characteristic value, the image used for measuring the characteristic value, and the number.

7. The endoscope device according to claim 6, wherein when the characteristic value exceeds a predetermined threshold value, the recording portion further records an index indicating that the characteristic value exceeds the threshold value.

8. The endoscope device according to claim 6, further comprising:
   a display portion that displays the image, wherein
   when the characteristic value exceeds a predetermined threshold value, the recording portion further records an index indicating that the characteristic value exceeds the threshold value,
   the display portion selectably displays a whole image corresponding to a number of blades, portions related to the characteristic value exceeding the threshold value, and the image.

9. The endoscope device according to claim 6, further comprising:
   a display portion that displays the image; and
   a characteristic value comparing portion, wherein the characteristic value comparing portion displays on the display portion the image and the characteristic value of the blade previously measured and the image and the characteristic value of the same blade currently measured which is arbitrarily selected by the measuring portion.

10. An endoscope device comprising:
an image capture portion that captures an image of an object that rotates in a circumferential direction around an axis;
a position detection portion embodied in a machine, the position detecting portion being configured to:
calculate a brightness component of image data associated with the image captured by the image capture portion; and
determine whether or not the object is at a position that enables the object to be image captured at least based on the brightness component of the image data, the brightness component resulting from the machine's analysis of the image data;
a measuring portion that measures a characteristic value of the object based on the image when the object is determined to be at a position that enables the object to be image captured by using the image captured by the image capture portion, and
a recording portion that records the characteristic value and the image used for measuring the characteristic value.

11. An inspection method comprising:
capturing an image of a blade provided in an engine;
calculating a brightness component of image data associated with the captured image; and
determining by a machine whether or not a blade is at a position that enables the blade to be image captured at least based on the brightness component of the image data, the brightness component resulting from the machine's analysis of the image data;
measuring a characteristic value of the blade based on the image when the blade is at a position that enables the blade to be image captured, and
recording the characteristic value and the image used for measuring the characteristic value.

12. The inspection method according to claim 11, further comprising:
providing the image with a number; and
recording the number together with the image used for measuring the characteristic value when the characteristic value exceeds a predetermined threshold value.

13. The inspection method according to claim 11, further comprising recording an index that indicates the characteristic value exceeding the threshold value together with the image used for measuring the characteristic value.

14. The inspection method according to claim 11, further comprising:
providing the image with a number;
recording an index that indicates the characteristic value exceeding the threshold value together with the number and the image used for measuring the characteristic value; and displaying selectably a whole image corresponding to a number of blades, portions related to the characteristic value exceeding the threshold value, and the image.

15. The inspection method according to claim 11, further comprising:
providing the image with a number;
recording the characteristic value and the number together with the image used for measuring the characteristic value; and
displaying on the display portion the image and the characteristic value of the blade previously measured and the image and the characteristic value of the same blade currently measured which is arbitrary selected by the measuring portion.

16. An endoscope device comprising:
an image capture portion that captures an image of a blade provided in an engine;
a position detection portion embodied in a machine that determines whether or not the blade is at a position that enables the blade to be image captured based upon the machine's analysis of image data associated with the image captured by the image capture portion;
a display portion that displays the image, wherein
the position detection portion determines whether or not the blade is at a position that enables the blade to be image captured by extracting two outlines with angles close to the transverse direction of the display portion displayed based on the image captured by the image capture portion and the position detection portion determines the blade to be at the position that enables the blade to be image captured when a center line in the horizontal direction of the display portion is set between the extracted two outlines.

17. An endoscope device comprising:
an image capture portion that captures an image of a blade provided in an engine;
a position detection portion embodied in a machine that determines whether or not the blade is at a position that enables the blade to be image captured based upon the machine's analysis of image data associated with the image captured by the image capture portion;
a display portion that displays the image, wherein
the position detection portion determines whether or not the blade is at a position that enables the blade to be image captured by extracting two outlines with angles close to the transverse direction of the display portion displayed based on the image captured by the image capture portion and the position detection portion determines the blade to be positioned in the position that enables the blade to be image captured, even when there are more than two outlines, if the center line in the horizontal direction of the display portion is set between the outlines.

* * * * *